US007560096B2

(12) United States Patent
Driehuys et al.

(10) Patent No.: US 7,560,096 B2
(45) Date of Patent: *Jul. 14, 2009

(54) DIAGNOSTIC PROCEDURES USING DIRECT INJECTION OF GASEOUS HYPERPOLARIZED $^{129}$XE AND ASSOCIATED SYSTEMS AND PRODUCTS

(75) Inventors: Bastiaan Driehuys, Durham, NC (US); Klaus D. Hagspiel, Charlottesville, VA (US)

(73) Assignee: Medi-Physics, Inc, Princeton, NJ (US)

( * ) Notice: Subject to any disclaimer, the term of this patent is extended or adjusted under 35 U.S.C. 154(b) by 419 days.

This patent is subject to a terminal disclaimer.

(21) Appl. No.: 10/617,326

(22) Filed: Jul. 10, 2003

(65) Prior Publication Data

US 2004/0143179 A1    Jul. 22, 2004

Related U.S. Application Data

(62) Division of application No. 09/804,369, filed on Mar. 12, 2001, now Pat. No. 6,630,126.

(60) Provisional application No. 60/189,072, filed on Mar. 13, 2000.

(51) Int. Cl.
*A61B 5/055* (2006.01)
(52) U.S. Cl. ............ 424/9.3; 424/1.11; 424/1.65; 424/1.81; 424/9.1; 424/9.2
(58) Field of Classification Search ........... 424/1.11, 424/1.65, 9.1, 9.3, 9.36; 534/7; 600/410, 600/420; 436/173
See application file for complete search history.

(56) References Cited

U.S. PATENT DOCUMENTS

| | | | |
|---|---|---|---|
| 3,623,474 A | 11/1971 | Hellman et al. | 128/2 R |
| 4,312,860 A | 1/1982 | Clements | 424/199 |
| 4,466,442 A | 8/1984 | Hilmann et al. | 128/653 |
| 4,586,511 A | 5/1986 | Clark, Jr. | 128/653 |
| 4,775,522 A | 10/1988 | Clark, Jr. | 424/9 |
| 4,793,357 A | 12/1988 | Lindstrom | 128/654 |
| 4,826,821 A | 5/1989 | Clements | 514/78 |
| 4,996,041 A | 2/1991 | Arai et al. | 424/9 |
| 5,046,498 A | 9/1991 | Fishman | 128/653 |
| 5,186,924 A | 2/1993 | Fishman | 424/9 |
| 5,190,744 A | 3/1993 | Rocklage et al. | 424/9 |
| 5,309,903 A | 5/1994 | Long | 128/203.12 |
| 5,322,511 A | 6/1994 | Armbruster et al. | 604/155 |
| 5,352,979 A | 10/1994 | Conturo | 324/307 |
| 5,438,982 A | 8/1995 | MacIntyre | 128/207.14 |
| 5,509,412 A | 4/1996 | Bahn | 128/653.2 |
| 5,522,390 A | 6/1996 | Tuithof et al. | 128/653.2 |
| 5,545,396 A | 8/1996 | Albert et al. | 424/93 |
| 5,617,859 A | 4/1997 | Souza et al. | 128/653.2 |
| 5,617,860 A | 4/1997 | Chupp et al. | 128/653.4 |
| 5,626,137 A | 5/1997 | Dumoulin et al. | 128/653.2 |
| 5,642,625 A | 7/1997 | Cates, Jr. et al. | 62/55.5 |
| 5,773,024 A | 6/1998 | Unger et al. | 424/450 |
| 5,785,953 A | 7/1998 | Albert et al. | 424/93 |
| 5,788,665 A | 8/1998 | Sekins | 604/19 |
| 5,789,921 A | 8/1998 | Albert et al. | 324/300 |
| 5,924,987 A | 7/1999 | Meaney et al. | 600/420 |

(Continued)

FOREIGN PATENT DOCUMENTS

EP    0 446 715 A2    9/1991

(Continued)

OTHER PUBLICATIONS

International Search Report corresponding to PCT/US 01/07812; date of mailing: Apr. 18, 2002.

(Continued)

*Primary Examiner*—D. L Jones
(74) *Attorney, Agent, or Firm*—Robert F. Chisholm

(57) ABSTRACT

A method of screening for pulmonary embolism uses gaseous phase polarized $^{129}$Xe which is injected directly into the vasculature of a subject. The gaseous $^{129}$Xe can be delivered in a controlled manner such that the gas substantially dissolves into the vasculature proximate to the injection site. Alternatively, the gas can be injected such that it remains as a gas in the bloodstream for a period of time (such as about 8-29 seconds). The injectable formulation of polarized $^{129}$Xe gas is presented in small quantities of (preferably isotopically enriched) hyperpolarized $^{129}$Xe and can provide high-quality vasculature MRI images or NMR spectroscopic signals with clinically useful signal resolution or intensity. One method injects the polarized $^{129}$Xe as a gas into a vein and also directs another quantity of polarized gas into the subject via inhalation. In this embodiment, the perfusion uptake allows arterial signal information and the injection (venous side) allows venous signal information. The dual delivery is used to generate a combined introduction path with a more complete image signal of both the arterial and venous side of the pulmonary vasculature. In this NMR imaging method, the pulmonary embolism screening method can use the same NMR chest coil for the excitation and detection of the $^{129}$Xe signals. The direct injection of small quantities of gas at particular sites along the vasculature targets specific target regions to provide increased signal intensity NMR images. The disclosure also includes related methods directed to other diagnostic vasculature regions physiological and conditions. Associated delivery and dispensing systems and methods, containers, and quantitative formulations of the polarized gas are also described.

6 Claims, 13 Drawing Sheets

U.S. PATENT DOCUMENTS

| | | | | |
|---|---|---|---|---|
| 5,934,103 | A | 8/1999 | Ryan et al. | 62/637 |
| 5,936,404 | A | 8/1999 | Ladebeck et al. | 324/300 |
| 5,968,017 | A | 10/1999 | Lampropoulos et al. | 604/183 |
| 6,023,162 | A | 2/2000 | Johnson | 324/300 |
| 6,033,645 | A | 3/2000 | Unger et al. | 424/9.5 |
| 6,042,809 | A | 3/2000 | Tournier et al. | 424/9.3 |
| 6,051,208 | A | 4/2000 | Johnson et al. | 424/9.3 |
| 6,085,743 | A | 7/2000 | Rosen et al. | 128/200.24 |
| 6,123,919 | A | 9/2000 | Albert et al. | 424/9.3 |
| 6,134,914 | A | 10/2000 | Eschwey et al. | 62/637 |
| 6,199,385 | B1 | 3/2001 | Driehuys et al. | |
| 6,237,363 | B1 | 5/2001 | Zollinger et al. | |
| 6,269,648 | B1 | 8/2001 | Hasson et al. | |
| 6,346,229 | B1 * | 2/2002 | Driehuys et al. | 424/9.36 |
| 6,370,415 | B1 | 4/2002 | Weiler et al. | 600/410 |
| 6,453,188 | B1 * | 9/2002 | Ardenkjaer-Larsen et al. | 600/420 |
| 6,491,895 | B2 * | 12/2002 | Driehuys et al. | 424/9.36 |
| 6,630,126 | B2 * | 10/2003 | Driehuys et al. | 424/9.3 |
| 6,696,040 | B2 * | 2/2004 | Driehuys | 424/9.3 |
| 6,808,699 | B2 * | 10/2004 | Driehuys et al. | 424/9.36 |
| 7,179,450 | B2 * | 2/2007 | Driehuys et al. | 424/9.36 |
| 7,357,917 | B2 * | 4/2008 | Driehuys | 424/9.3 |

FOREIGN PATENT DOCUMENTS

| | | |
|---|---|---|
| EP | 0 547 463 A1 | 6/1993 |
| EP | 0933062 A2 | 8/1999 |
| WO | WO 97/37239 | 10/1997 |
| WO | WO98/43701 | 10/1998 |
| WO | WO98/58272 | 12/1998 |
| WO | WO 99/07415 | 2/1999 |
| WO | WO99/08941 | 2/1999 |
| WO | WO 99/25243 | 5/1999 |
| WO | WO99/35508 | 7/1999 |
| WO | WO 99/47940 | 9/1999 |
| WO | WO 99/52428 | 10/1999 |
| WO | WO99/53332 | 10/1999 |
| WO | WO 99/66254 | 12/1999 |
| WO | WO 99/66255 | 12/1999 |
| WO | WO 00/21601 | 4/2000 |
| WO | WO 00/23797 | 4/2000 |
| WO | WO00/40972 | 7/2000 |
| WO | WO 01/74246 | 10/2001 |
| WO | WO 02/04709 | 1/2002 |

OTHER PUBLICATIONS

Albert et al., "$^{129}$Xe Relaxation Catalysis by Oxygen", Abstracts of the 11th Annual Meetings of the Society for Magnetic Resonance Medicine, Abstract No. 4710 (1992).

Albert et al., "Aqueous Shift Reagents for High-resolution Cation NMR. VI," Reprint from NMR in Biomedicine 6 7-20 (1993).

Albert et al., "Biological magnetic resonance imaging using laser-polarized $^{129}$Xe," Letters to Nature, vol. 370, pp. 199-201 (Jul. 21, 1994).

Albert et al., "Magnetic Resonance Imaging Using Hyperpolarized $^{129}$Xe," Medical Electronics, pp. 72-80 (Dec. 1994).

Albert et al., "Relaxation of $^{129}$Xe in Model Biological Systems: On Probing the Mechanism of General Anesthesia", Abstracts of the 11th Annual Meetings of the Society for Magnetic Resonance Medicine, Abstract No. 2104 (1992).

Albert et al., "Susceptibility Changes Following Bolus Injections," Reprint from Magnetic Resonance in Medicine 29 700-708 (1993).

Albert et al., "Development of Hyperpolarized Noble Gas MRI," Nucl. Inst. And Meth. In Phys. Res. A 402, pp. 441-453 (1998).

Albert et al., "Measurement of $^{129}$Xe T1 in Blood to Explore the Feasibility of Hyperpolarized $^{129}$Xe MRI," Jour. Comp. Ass. Tomography, vol. 19, No. 6 (Nov.-Dec. 1995).

Augustine et al., "Low Field Magnetic Resonance Images of Polarized Noble Gases Obtained with a dc Quantum Interference Device," App. Phys. Ltrs., vol. 72, No. 15, pp. 1908-1910 (Apr. 1998).

Bárány, M. et al., "High Resolution Proton Magnetic Resonance Spectroscopy of Human Brain and Liver," Magn. Reson. Imaging, 5:393 (1987).

Becker et al., "Study of Mechanical Compression of Spin-Polarized $^3$He Gas", Nuclear Instruments and Methods In Physics Research, vol. A 346, pp. 45-51 (1994).

Belliveau et al., "Functional Cerebral Imaging by Susceptibility-Contrast NMR," 14 Magnetic Resonance in Medicine 14, pp. 538-546 (1990).

Bhaskar et al., "Efficiency of Spin Exchange between Rubidium Spins and $^{129}$Xe Nuclei in a Gas", Physical Review Letters, vol. 49, No. 1, pp. 25-28 (Jul. 5, 1982).

Bifone, et al., "NMR of laser-polarized xenon in human blood," Proc. Natl. Acad. Sci. USA, vol. 93, pp. 12932-12936 (Nov. 1996).

Blumgart et al., "Studies on the Velocity of Blood Flow," J. Clin. Invest., 4:339-425 (1927).

Borman, "Xenon Used to Expand Magnetic Imaging," Chem. & Eng. News, vol. 72, No. 30, pp. 7-8 (Jul. 25, 1994).

Brookeman, J.R., "MRS and MRI of Hyperpolarized $^{129}$Xe: Studies in Human Volunteers," pp. 505-512, Proceedings of Educational Course at the Sixth Meeting of the International Society for Magnetic Resonance in Medicine, Sydney, Australia (Apr. 1998).

Burt et al., "Fluorinated Anesthetics as Probes of Lipophilic Environments in Tumors," J. Magn._Reson., 53:163 (1983).

Burt et al., "The Fluorinated Anesthetic Halothane as a Potential NMR Biologic Probe," Biochem. Biophys. Acta., 805:375 (1984).

Chawla, et al., "In Vivo Magnetic Resonance Vascular Imaging Using Laser-Polarized 3He Microbubbles," Proc. Natl. Acad. Sci, vol. 95, pp. 10832-10835 (Sep. 1998).

Chupp et al., "Chemical Shift Imaging of Laser-Polarized $^{129}$XE Magnetization in Rats In Vivo," European Radiology, 9:B45 (1999).

de Lange et al., "Lung Airspaces: MR Imaging Evaluation with Hyperpolarized Helium-3 Gas," Radiology 210, 851-857(1999).

Diehl et al., "Nuclear Magnetic Relaxation of the $^{129}$Xe and $^{131}$Xe Isotopes of Xenon Gas Dissolved in Isotropic and Anisotropic Liquids," J. Magn. Reson., vol. 88, pp. 660-665 (1990).

Donnelly et al., "Cystic Fibrosis: Combined Hyperpolarized 3He-enhanced and Conventional Proton MR Imaging in the Lung—Preliminary Observations," Radiology 212, pp. 885-889(Sep. 1999).

Driehuys et al., "High-volume production of laser-polarized $^{129}$Xe", Appl. Phys. Lett., vol. 69, No. 12, pp. 1668-1670 (Sep. 16, 1996).

Driehuys et al., "Surface Relaxation Mechanisms of Laser-Polarized 129Xe," 74 Phys. Rev. Lett., No. 24, pp. 4943-4946 (Jun. 12, 1995).

Fullerton et al., Chapter 3 "Relaxation of Biological Tissues," Biomedical Magnetic Resonance Imaging: Principles, Methodology, and Applications, pp. 115-155, (1988).

Gao et al., "Magnetization and Diffusion Effects in NMR Imaging of Hyperpolarized Substances," Mag. Reson. in Med., vol. 37, No. 1, pp. 153-158 (Jan. 1997).

Glover et al., Research Directions in MR Imaging[1], Radiology, vol. 207, pp. 289-295, (1998).

Goodson et al., "In vivo NMR and MRI Using Injection Delivery of Laser-Polarized Xenon," 94 Proc. Natl. Acad. Sci. USA, pp. 14725-14729 (1997).

Horbar et al., "A Multicenter Randomized, Placebo-controlled Trial of Surfactant Therapy for Respiratory Distress Syndrome," 320 The New England Jnl. of Med., No. 15, pp. 959-965 (Apr. 13, 1989).

Hou, et al., "Optimization of Fast Acquisition Methods for Whole-Brain Relative Cerebral Blood Volume (rCBV) Mapping with Susceptibility Contrast Agents," J. Mag. Res. Imaging, vol. 9 pp. 233-239 (1999).

Il'yasov et al., "129Xe NMR in Study of Tissues and Plants," Appl. Magn. Reson. vol. 17, pp. 17-84 (1999).

Kaatz et al., "A comparison of molecular hyperpolarizabilities from gas and liquid," J. Chem. Phys., vol. 108, No. 3, pp. 849-856 (Jan. 15, 1998).

Kauczor et al., "MRI Using Hyperpolarized Noble Gases," Eur. Radiol., vol. 8, No. 5, Abstract (1998).

Kendall et al., "Xenon as a Contrast Agent for Computed Tomography," J. Neuroradiology, vol. 8, No. 3, pp. 3-12 (1981).

Kerns et al., "Carbon Dioxide Digital Subtraction Angiography: Expanding Applications and Technical Evolution," 164 Am. Jnl. Roentgen., pp. 735-741 (1995).

Knudsen et al., "Blood-brain barrier permeability measurements by double-indicator method using intravenous injection," Am. J. Physiol. 266 (Heart Circ. Physiolo. 35) pp. H987-H999 (1994).

Lassen, "Cerebral Transit of an Intravascular Tracer May Allow Measurement of Regional Blood Volume But Not Regional Blood Flow," 4 J. Cereb. Blood Flow and Metab. pp. 633-634 (1984).

Le Bihan, "Magnetic Resonance Imaging of Perfusion*," Mag. Reson. In Med., vol. 14, pp. 283-292 (1990).

MacFall et al., "Human Lung Air Spaces: Potential for MR Imaging with Hyperpolarized He-3[1]," Radiology, vol. 200, No. 2, pp. 553-558 (1996).

Mair et al., "Magnetic Resonance Imaging of Convection in Laser-Polarized Xenon," Phys. Rev. E, vol. 61, No. 3 (Mar. 2000).

Mair et al., "Probing Porous Media with Gas Diffusion NMR," Phys. Rev. Ltrs., vol. 83, No. 16, pp. 3324-3327 (Oct. 18, 1999).

Mansfeld et al., "The Use of $^{129}$Xe NMR exchange spectroscopy for probing the microstructure of porous materials," Chem. Phys. Ltrs., vol. 213, No. 1, 2, pp. 153-157 (Oct. 1, 1993).

Martin, "The Pharmacokinetics of Hyperpolarized Xenon: Implications for Cerebral MRI," Jour. Magn. Reson. Imag., vol. 7, No. 5, pp. 848-854 (Sep.-Oct. 1997).

Mazitov et al. "A Simple method for producing liquid or solid NMR samples containing dissolved gases at elevated pressures," Rev. Sci. Instrum. 65 (6), pp. 21492150 (Jun. 1994).

McAdams et al., "Hyperpolarized 3 He-Enhanced MR Imaging of Lung Transplant Recipients: Preliminary Results," AJR 173, 955-959 (1999).

McKim et al., "Evidence of xenon transport through the gramicidin channel: a $^{129}$Xe-NMR study," Biochimica et Biophysica Acta 1193, pp. 186-198 (1994).

Miller et al., "Xenon NMR: Chemical shifts of a general anesthetic common solvents, proteins, and membranes", Proc. of the Nat. Acad. of Sci. (USA), vol. 78, No. 8, pp. 4946-4949 (Aug. 1981).

Miller, "$^{129}$Xe NMR in Polymers," Rubber Chem. And Tech., vol. 66, pp. 455-461 (1993).

Möller et. al., "Magnetic Resonance Angiography with Hyperpolarized 129Xe Dissolved in Lipid Emulsion," 41 Mag. Res. Med. No. 5, pp. 1058-1064 (1999).

Moschos, A. et al., "Communications Nuclear Magnetic Relaxation of Xenon-129 Dissolved in Organic Solvents," J. Mag. Reson., vol. 95, pp. 603-606 (1991).

Moseler et al, "Formation, Stability, and Breakup of Nanojets, Science," vol. 289, No. 5482, pp. 1165-1169 (Aug. 18, 2000).

Mugler, III et al. Gradient-Echo MR Imaging, RSNA Categorical Course in Physics: The Basic Physics of MR Imaging[1], U. of VA Health Sci. Ctr., pp. 71-88 (1997).

Mugler, III et al., "MR Imaging and Spectroscopy Using Hyperpolarized 129Xe Gas: Preliminary Human Results," 37 Magn. Reson. In Med., vol. 37, No. 6, pp. 809-815 (1997).

Navon et al., "Enhancement of Solution NMR and MRI with Laser-Polarized Xenon," Science, vol. 271, pp. 1848-1851 (Mar. 1996).

Pasquier et al., "$^{129}$Xe NMR as a Probe of the Dynamics of Gas Confined Porous Vycor," Mag. Reson. Imag., vol. 14, No. 7/8, pp. 971-973 (1996).

Patyal, "Longitudinal Relaxation and Diffusion Measurements Using Magnetic Resonance Signals from Laser-Hyperpolarized $^{129}$Xe Nuclei," J. Magn. Reson., vol. 126, No. 1, pp. 58-65, May 1997.

Peled et al., "Determinants of Tissue Delivery for $^{129}$Xe Magnetic Resonance in Humans," Mag. Res. Med, vol. 36, pp. 340-343 (1996).

Pfeffer et al., "$^{129}$Xe gas NMR spectroscopy and imaging with a whole-body imager," J. Mag. Reson., Ser. A., vol. 108, No. 1, pp. 106-109 (May 1994).

Pietraβ et al., "Optically Polarized 129Xe in NMR Spectroscopy," Advanced Materials, pp. 826-838 (1995).

Pollack et al., "Solubility of xenon in liquid n-alkanes: Temperature dependence and thermodynamic functions," J. Chem. Phys., vol. 7, No. 6, pp. 3221-3229 (Sep. 15, 1982).

Pollack et al., "Solubility of xenon in liquid n-alkanois: Thermodynamic functions in simple polar liquids," J. Chem. Phys., 81 (7) pp. 3239-3246 (Oct. 1, 1984).

Presson et al., "Fate of Air Emboli in the Pulmonary Circulation," 67 J. Appl. Physiol. 5, pp. 1898-1902 (1989).

Raftery, et al. , "High-Field NMR of Adsorbed Xenon Polarized by Laser Pumping," Phys. Rev. Lett., vol. 66, No. 5, pp. 584-587 (Feb. 4, 1991).

Raftery, et al., "NMR of optically pumped xenon thin films," Chem. Phys. Lett., vol. 191, No. 5, pp. 385-390 (Apr. 8, 1992).

Ratanakorn et al., "A New Dynamic Method for Detection of Internal Jugular Valve Incompetence Using Air Contrast Ultrasonography," Jn. of Neuroimaging, vol. 9, No. 1, pp. 10-14 (Jan. 1999).

Rosen et al., "Perfusion Imaging by Nuclear Magnetic Resonance," Mag. Reson. Quart., vol. 5, No. 4, pp. 263-281 (1989).

Rosen et al., Polarized $^{129}$Xe optical pumping/spin exchange and delivery system for magnetic resonance spectroscopy and imaging studies, Rev. Sci. Instrum., vol. 70, No. 2, pp. 1546-1552 (Feb. 1999).

Ruppert et al., "NMR of hyperpolarized $^{129}$Xe in the canine chest: spectral dynamics during a breath-hold," NMR Biomed., vol. 13, pp. 220-228 (2000).

Ruth et al., "Production of Nitrogen-Free, Hyperpolarized $^{129}$Xe Gas," Appl. Phys. B, vol. 68, pp. 93-97 (1999).

Sauer et al., "Laser-Polarized Liquid Xenon," Chem. Phys. Lett., vol. 277, pp. 153-158 (Oct. 3, 1997).

Schad et al., "Hyperpolarized Gases—A New Type of MR Contrast Agents?," Acta Radiologica 38, Suppl. 412, pp. 43-46 (1997).

Schoenborn, "Binding of Xenon to Horse Haemoglobin," Nature, vol. 208, pp. 760-762 (Nov. 20, 1965).

Song et al., "Effects of Diffusion on Magnetic Resonance Imaging of Laser-Polarized Xenon Gas," Jour. Chem. Phys., vol. 108, No. 15, pp. 6233-6239 ( Apr. 1998).

Song et al., "Spin-Polarized $^{129}$Xe Gas Imaging of Materials," J. Mag. Reson., Series A 115, pp. 127-130 (1995).

Swanson et al., "Brain MRI with Laser-Polarized $^{129}$Xe," Mag. Res. Med., vol. 38, pp. 695-698 (1997).

Tilton, Jr., et al., "Nuclear Magnetic Resonance Studies of Xenon-129 with Myoglobin and Hemoglobin," Biochemistry, vol. 21, No. 26, pp. 6850-6857 (1982).

Tseng et al., "NMR of Laser-Polarized $^{129}$Xe in Blood Foam," J. Mag. Res., vol. 126, pp. 79-86 (1997).

van Blankenstein et al., "Cardiac Depression after Experimental Air Embolism in Pigs: Role of Addition of a Surface-Active Agent", 34 Cardiovascular Research, pp. 473-482 (1997).

van Blankenstein et al., "Heart Function after Injection of Small Air Bubbles in Coronary Artery of Pigs," 67 J. App. Physiol. 5, pp. 1898-1902 (1989).

Wagshul, "In Vivo MR Imaging and Spectroscopy Using Hyperpolarized 129Xe," Mag. Reson. Med., vol. 36, No. 2, pp. 183-191 (Aug. 1996).

Wagshul et al., "Optical Pumping of High-Density Rb With a Broadband Dye Laser and GaA1As Siode Laser Arrays: Application to $^3$He Polarization," Phys. Rev. A., vol. 40, No. 8, pp. 4447-4454 (1989).

Wolber et al., "Perfluorocarbon Emulsions as Intravenous Delivery Media for Hyperpolarized Xenon," 41 Mag. Res. Med., pp. 442-449 (1999).

Wolber et al., "Spin-lattice relaxation of laser-polarized xenon in human blood," 96 Proc. Natl. Acad. Sci. USA, pp. 3664-3669 (Mar. 1999).

Yen, W.M. et al., "Nuclear Magnetic Resonance of Xe129 in Solid and Liquid Xenon," Phys. Rev., 131:269 (1963).

Yonas, H. et al., "Determination of Irreversible Ischemia by Xenon-Enhanced Computed Tomographic Monitoring of Cerebral Blood flow in Patients with Symptomatic Vasospasm," Neurosurgery, vol. 24, pp. 368-372 (Mar. 1989).

Zeng et al., "Wall Relaxation of Spin Polarized $^{129}$Xe Nuclei," Phys. Ltrs., vol. 96A, No. 4 (Jun. 27, 1983).

Zeng et al., "Experimental determination of the rate constants for spin exchange between optically pumped K, Rb, and Cs atoms and $^{129}$Xe nuclei in alkali-metal—noble-gas van der Waals molecules," Physical Review A, vol. 31, No. 1, pp. 260-278 (Jan. 1985).

* cited by examiner

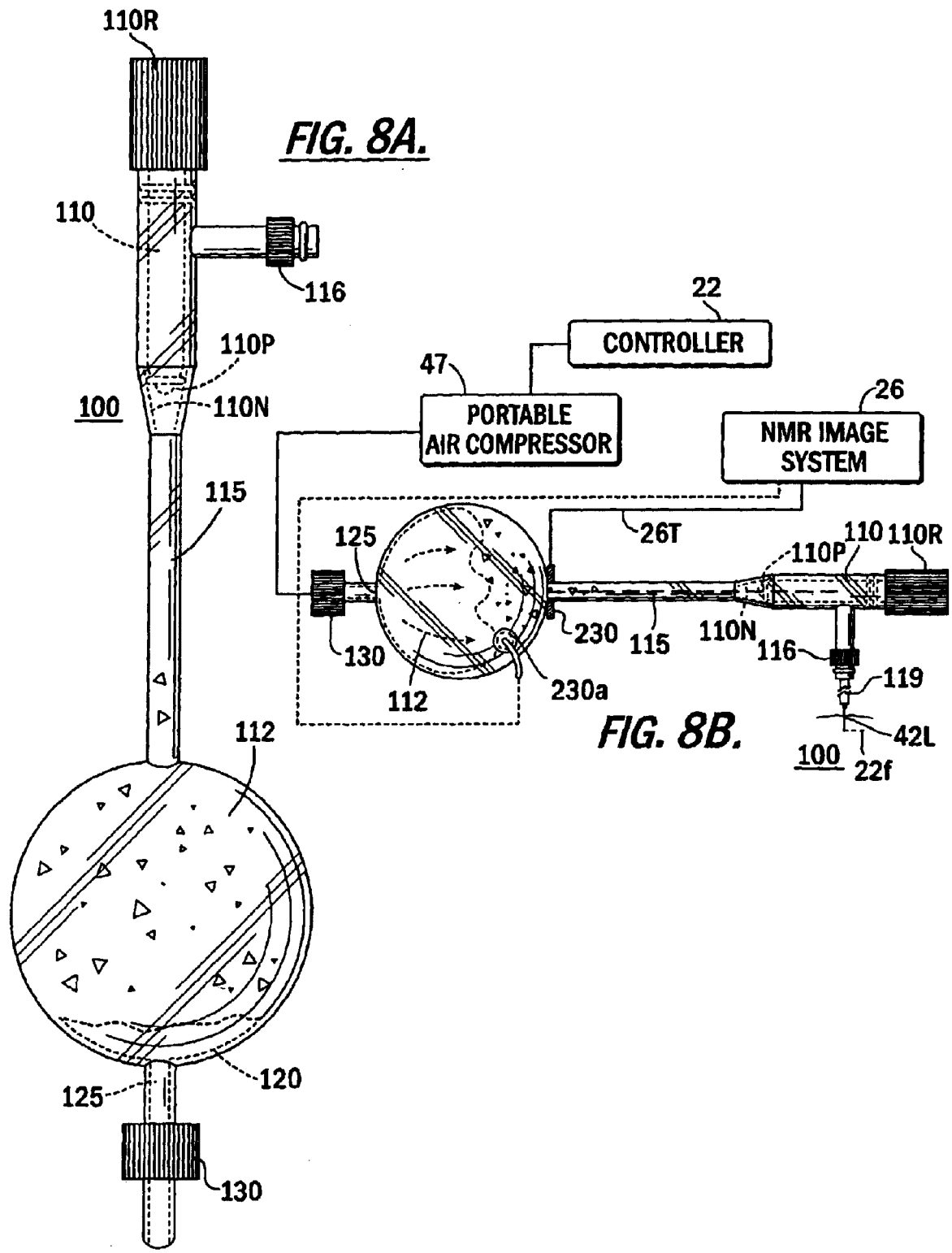

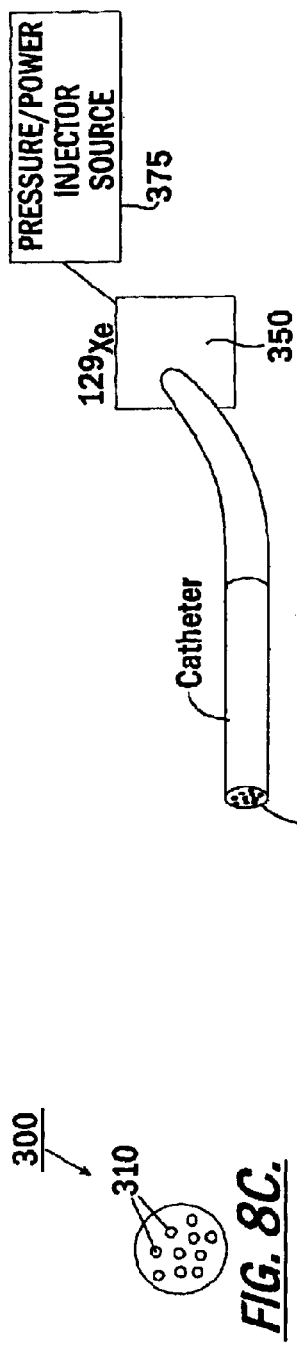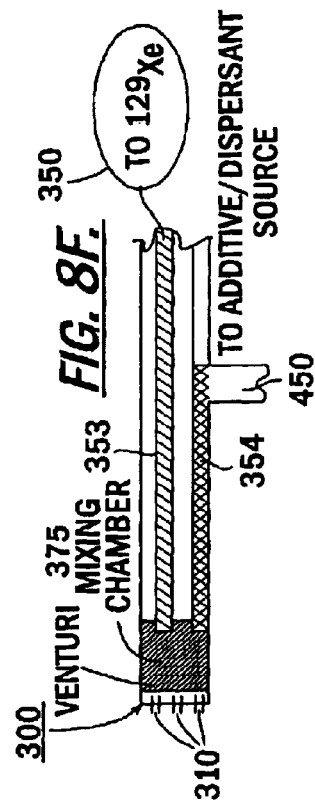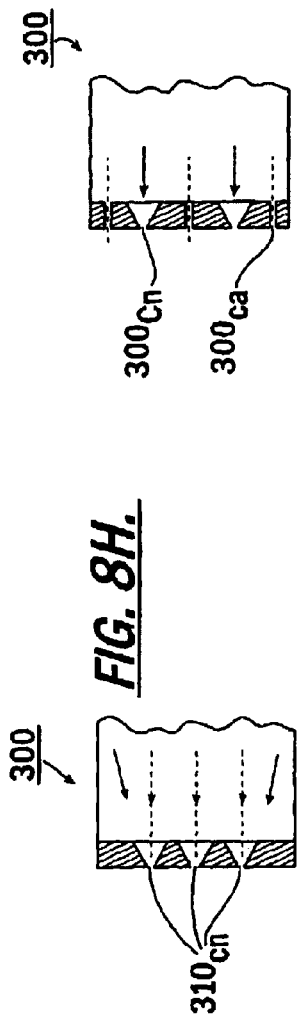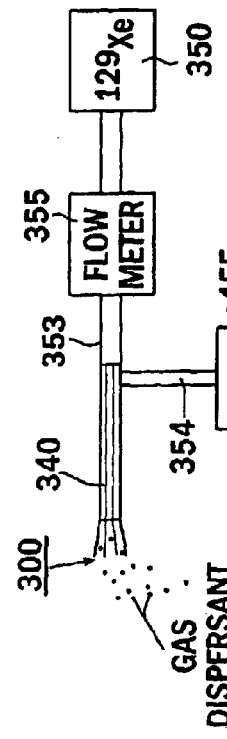

DIAGNOSTIC PROCEDURES USING DIRECT INJECTION OF GASEOUS HYPERPOLARIZED $^{129}$XE AND ASSOCIATED SYSTEMS AND PRODUCTS

RELATED APPLICATIONS

This application is a divisional of application Ser. No. 09/804,369 filed Mar. 12, 2001, issued as U.S. Pat. No. 6,630, 126, which claims priority benefit of U.S. provisional patent application Ser. No. 60/189,072 filed Mar. 13, 2000, the entire disclosure of which is hereby incorporated by reference.

FIELD OF THE INVENTION

The present invention relates generally to magnetic resonance imaging ("MRI") and spectroscopy methods, and more particularly to the use of hyperpolarized $^{129}$Xe in MRI and spectroscopy.

BACKGROUND OF THE INVENTION

MRI using hyperpolarized noble gases has been demonstrated as a viable imaging modality. See e.g., U.S. Pat. No. 5,545,396 to Albert et al. The contents of this patent are hereby incorporated by reference as if recited in full herein. Albert et al. proposed several techniques of introducing the hyperpolarized gas (either alone or in combination with another substance) to a subject, such as via direct injection, intravenous injection, and inhalation. See also *Biological magnetic resonance imaging using laser-polarized* $^{129}$Xe, 370 Nature, pp. 199-201 (Jul. 21, 1994). Other researchers have since obtained relatively high-quality images of the lung using pulmonary ventilation of the lung with both hyperpolarized $^3$He and $^{129}$Xe. See J. R. MacFall, H. C. Charles, R. D. Black, H. Middleton, J. Swartz, B. Saam, B. Driehuys, C. Erickson, W. Happer, G. Cates, G. A. Johnson, and C. E. Ravin, "*Human lung air spaces: Potential for MR imaging with hyperpolarized He-3,*" Radiology 200, 553-558 (1996); and Mugler et al., *MR Imaging and spectroscopy using hyperpolarized 129Xe gas: Preliminary human results,* 37 Mag. Res. Med., pp. 809-815 (1997). See also E. E. de Lange, J. P. Mugler, J. R. Brookeman, J. Knight-Scott, J. Truwit, C. D. Teates, T. M. Daniel, P. L. Bogorad, and G. D. Cates, "*Lung Airspaces: MR Imaging Evaluation with Hyperpolarized Helium-3 Gas,*" Radiology 210, 851-857(1999); L. F. Donnelly, J. R. MacFall, H. P. McAdams, J. M. Majure, J. Smith, D. P. Frush, P. Bogorad, H. C. Charles, and C. E. Ravin, "*Cystic Fibrosis: Combined Hyperpolarized 3He-enhanced and Conventional Proton MR Imaging in the Lung—Preliminary Observations,*" Radiology 212 (September 1999), 885-889 (1999); H. P. McAdams, S. M. Palmer, L. F. Donnelly, H. C. Charles, V. F. Tapson, and J. R. MacFall, "*Hyperpolarized 3He-Enhanced MR Imaging of Lung Transplant Recipients: Preliminary Results,*" AJR 173, 955-959 (1999).

In addition, due to the high solubility of $^{129}$Xe in blood and tissues, vascular and tissue imaging using inhaled hyperpolarized $^{129}$Xe has also been proposed. Generally described, during inhalation delivery, a quantity of hyperpolarized $^{129}$Xe is inhaled by a subject (a subject breathes in the $^{129}$Xe gas) and the subject then holds his or her breath for a short period of time, i.e., a "breath-hold" delivery. This inhaled $^{129}$Xe gas volume then exits the lung space and is generally taken up by the pulmonary vessels and associated blood or pulmonary vasculature at a rate of approximately 0.3% per second. For example, for an inhaled quantity of about 1 liter of hyperpolarized $^{129}$Xe, an estimated uptake is about 3 cubic centimeters per second or a total quantity of about 40 cubic centimeters of $^{129}$Xe over about a 15 second breath-hold period. Accordingly, it has been noted that such uptake can be used to generate images of pulmonary vasculature or even organ systems more distant from the lungs. See co-pending and co-assigned U.S. patent application Ser. No. 09/271,476 to Driehuys et al, entitled *Methods for Imaging Pulmonary and Cardiac Vasculature and Evaluating Blood Flow Using Dissolved Polarized* $^{129}$Xe. Although primarily directed to inhalation delivery, this application also proposes injection of $^{129}$Xe to replace conventional radioactive tracers in perfusion imaging methods. The contents of this application are hereby incorporated by reference as if recited in full herein.

Many researchers are also interested in the possibility of using inhaled $^{129}$Xe for imaging white matter perfusion in the brain, renal perfusion, and the like. While the inhaled delivery $^{129}$Xe methods are suitable, and indeed, preferable, for many MRI applications for several reasons, such as the non-invasive characteristics attendant with such a delivery to a human subject, it may not be the most efficient method to deliver a sufficiently large dose to more distant (away from the pulmonary vasculature which is proximate to the lungs) target areas of interest. In addition, due to the dilution of the inhaled $^{129}$Xe along the perfusion delivery path, relatively large quantities of the hyperpolarized $^{129}$Xe are typically inhaled in order to deliver a small fraction of the gas to the more distal target sites or organ systems. For example, the brain typically receives only about 13% of the total blood flow in the human body. Thus, the estimated 40 cubic centimeter quantity of hyperpolarized $^{129}$Xe taken up into the pulmonary vessels from the 1-liter inhalation dose can be reduced to only about 5 cubic centimeters by the time it reaches the brain.

Further, the hyperpolarized state of the gas is sensitive and can decay relatively quickly due to a number of relaxation mechanisms. Indeed, the relaxation time (generally represented by a decay constant "$T_1$") of the $^{129}$Xe in the blood, absent other external depolarizing factors, is estimated at $T_1=4.0$ seconds for venous blood and $T_1=6.4$ s for arterial blood at a magnetic field strength of about 1.5 Tesla. See Wolber et al., *Spin-lattice relaxation of laser-polarized xenon in human blood,* 96 Proc. Natl. Acad. Sci. USA, pp. 3664-3669 (March 1999). (The more oxygenated arterial blood provides increased polarization life over the relatively deoxygenated venous blood). Therefore, for about a 5 second transit time (the time estimate for the uptaken hyperpolarized $^{129}$Xe to travel to the brain from the pulmonary vessels), the $^{129}$Xe polarization is reduced to about 37% of its original value. In addition, the relaxation time of the polarized $^{129}$Xe in the lung itself is typically about 20-25 seconds due to the presence of paramagnetic oxygen. Accordingly, $^{129}$Xe taken up in the latter portion of the breath-hold cycle can decay to have only about 50% of the starting polarization (the polarization level at the initial portion of the breath hold cycle). Thus, generally stated, the average polarization of $^{129}$Xe entering the pulmonary blood can be estimated to be at about 75% of the starting inhaled polarization value. Taking these effects into account, the delivery to the brain of the inhaled $^{129}$Xe can be estimated as about 1.4 cubic centimeters of the inhaled one-liter dose of $^{129}$Xe polarized to the same level as the inhaled gas (0.75×0.37×5 cc's). This dilution reduces delivery efficiency, i.e., for remote target areas (such as the brain), the quantity of delivered $^{129}$Xe is typically severely reduced to only about 0.14% of the inhaled $^{129}$Xe. Nonetheless, at least one researcher has made coarse images of $^{129}$Xe in rat brains, but this inhalation administration delivery required large quantities of $^{129}$Xe to be inhaled over a relatively long period of time. See Swanson et al., *Brain MRI with* laser-polarized xenon in human blood, 38 Mag. Reson. Med., pp. 695-698 (1997). Unfortunately, the extended inhalation time period and/or associated large quantity dosage of the gas may not be desirable for certain clinical applications.

In an alternative delivery mode, Bifone et al. proposes the use of injectable formulations to deliver hyperpolarized $^{129}Xe$ to regions of interest. Bifone et al., *NMR of laser polarized xenon in human blood,* 93 Proc. Natl. Acad. Sci. USA No. 23, pp. 12932-12936 (1996). Albert et al., supra, also describes such formulations. As described by Bifone et al., the injectable formulation consists of a biocompatible fluid in which hyperpolarized $^{129}Xe$ is dissolved. Such formulations can then be injected intravenously to deliver hyperpolarized $^{129}Xe$. For fluid injection, the formulation is described as preferably formed such that the biocompatible fluid has a high solubility for xenon while also providing a relatively long $^{129}Xe$ relaxation time. Examples of particular suggested biocompatible fluids include saline, lipid emulsions, and perfluorocarbon emulsions. Several researchers have shown images of fluid injectable formulations. For example, Goodson et al. have shown images of $^{129}Xe$ dissolved in saline and injected into the hind leg of a rat. Goodson et al., *In vivo NMR and MRI Using Injection Delivery of Laser-Polarized Xenon,* 94 Proc. Natl. Acad. Sci. USA, pp. 14725-14729 (1997). Moeller et al. have also recently demonstrated venous angiography with hyperpolarized $^{129}Xe$ dissolved in Intralipid® solution. Moeller et. al., *Magnetic Resonance Angiography with Hyperpolarized 129Xe Dissolved in Lipid Emulsion,* 41 Mag. Res. Med. No. 5, pp. 1058-1064 (1999). The Intralipid® formulation purportedly has a xenon-Otswald solubility of about 0.6 and a $^{129}Xe$ relaxation time of 25 seconds in a magnetic field strength of 2.0 Tesla. In addition, Wolber et al, have also recently demonstrated PFOB (perfluorooctyl bromide) emulsions which allegedly have increased transverse relaxation times and have purportedly provided improved imaging results. Wolber et al., *Perfluorocarbon Emulsions as Intravenous Delivery Media for Hyperpolarized Xenon,* 41 Mag. Res. Med., pp. 442-449 (1999). In yet another injection technique, Chawla et al., have proposed the use of hyperpolarized $^3He$ microbubbles suspended in a hexabrix solution to perform angiography on rats. Chawla et al., *In Vivo Magnetic Resonance Vascular Imaging Using Laser-Polarized 3He Microbubbles,* 95 Proc. Natl. Acad. Sci. USA, pp. 10832-10835 (1998).

Unfortunately, many injectable formulations can be unduly susceptible to handling and processing variables which can negatively impact the injectable formulation's commercial viability and/or clinical application. For example, the relatively short (and potentially magnetic-field dependent) relaxation time of the $^{129}Xe$ in the injectable solutions can require that the $^{129}Xe$ gas be dissolved into the biocompatible fluid relatively quickly and then subsequently rapidly injected to reduce the polarization loss of the formulation prior to injection. In addition, it may be difficult to predict the dissolution efficiency in a manner which can provide a reliable xenon dissolution concentration. Unreliable concentrations can, unfortunately, yield widely varying signal intensities, dose to dose. Further, because of the typically relatively quick decay associated with these formulations, a careful measurement of the final $^{129}Xe$ polarization just prior to injection to determine the post dissolution polarization may not be possible. Still further, because the $^{129}Xe$ is dissolved in a biocompatible fluid, sensitivity to the local in vivo environment such as blood oxygenation, tissue type, and the like, may be muted, reduced, or even non-existent. The use of such fluids or carrier agents to deliver $^{129}Xe$ to selected tissues or organs can also be difficult because of the high solubility of $^{129}Xe$ in the fluid compared to the tissues (its preferred affinity being to remain in the fluid rather than to migrate into the selected or targeted tissues).

In view of the foregoing, and despite the present efforts, there continues to be a need to improve the methods, products, and systems used to deliver hyperpolarized $^{129}Xe$ gas to a target in vivo imaging region of interest.

OBJECTS AND SUMMARY OF THE INVENTION

It is therefore an object of the present invention to formulate and deliver $^{129}Xe$ in vivo in a manner which allows for high-quality mammalian tissue, organ, vascular, and/or angiographic MRI images using hyperpolarized gaseous $^{129}Xe$.

It is another object of the present invention to provide a method of using reduced quantities of hyperpolarized gas while providing increased MRI image signal resolution.

It is an additional object of the present invention to provide methods for obtaining improved quality NMR signals and/or MRI images of both the arterial and venous portions of the human vasculature and/or organs and/or systems using hyperpolarized $^{129}Xe$.

It is a further object of the present invention to provide appropriate (bolus) sized containers and associated delivery systems, apparatus, and methods which can reduce the depolarization of the hyperpolarized $^{129}Xe$ gas prior to and during delivery and can, thus, yield a clinically useful $T_1$.

It is another object of the present invention to introduce a sufficient quantity of hyperpolarized $^{129}Xe$ gas into the vasculature in a minimally intrusive manner to obtain MR spectroscopic signal and/or in vivo images.

It is yet another object of the present invention to facilitate the dissipation or dispersion of bubbles which may be injected into a subject.

It is an additional object of the present invention to provide imaging methods which may be able to screen for the presence of pulmonary emboli.

It is still another object of the invention to formulate $^{129}Xe$ as a pharmaceutical grade injectable formulation which can be monitored for polarization efficacy just prior to use with reduced decaying effect thereon.

It is another object of the present invention to provide NMR-based diagnostic capability of vasculature (arterial and/or venous or organ) circulation related defects or emboli in a minimally or non-invasive and effective manner.

It is yet another object of the present invention to provide a diagnostic tool for the evaluation of pharmaceutical effectiveness on drugs directed to target regions or functions.

It is an additional object of the present invention to provide in vivo diagnostic information regarding the cancerous condition of a solid mass.

It is another object of the present invention to prepare gas contacting surfaces and containers in a manner which reduces the amount of depolarizing oxygen therein while also employing purge gas which is suitable for injection.

It is still an additional object of the present invention to provide a way to optimize capillary length for improved polarization life in containers configured to hold polarized noble gases such as $^{129}Xe$ and/or $^3He$.

These and other objects of the present invention are provided by directly injecting in vivo a predetermined quantity of hyperpolarized $^{129}Xe$ in gaseous phase to obtain MR based spectroscopic signal or images regarding a target site in the mammalian vasculature (or target organ, tissue, or region). The present invention also includes delivery and dispensing methods, systems, and product formulations, as well as administration rates which may correspond to the use or injection site. In addition, the present invention provides polarization monitoring of the hyperpolarized gaseous $^{129}$Xe which is formulated for direct injection in vivo into the vasculature for MR imaging and spectroscopic analysis.

In particular, a first aspect of the present invention is directed toward the detection or screening for the presence of a pulmonary embolism. The method includes the step of positioning a subject having a pulmonary region and a blood circulation path including veins and arteries in a NMR system. The subject's pulmonary region has pulmonary veins and pulmonary arteries and associated vasculature defining a pulmonary portion of the circulation path. A quantity of polarized gaseous $^{129}$Xe is injected directly into at least one vein of the subject. NMR signal data associated with the polarized $^{129}$Xe in the pulmonary region of the subject is obtained. The signal data includes information corresponding to the polarized gas introduced in the injecting step. An MRI image is generated having spatially coded visual representation of the NMR signal data. The, presence of at least one condition of blockage, restriction, abnormality, and substantially unobstructed free passage of the pulmonary circulation path is identified.

In one embodiment, the quantity of venous injected gaseous $^{129}$Xe is less than about 100 cubic centimeters while quantity of arterial injected gaseous $^{129}$Xe is less than about 14-20 cc's.

In another embodiment, in order facilitate bubble dissipation which may be associated with the injection of the $^{129}$Xe gas within the subject, a quantity of liquid surfactant can be introduced in vivo temporally and spatially proximate to the gas injection (or concurrently at a location proximate to the gas injection) site. The injection pressure and/or the rate of injection can also be substantially controlled to thereby control the delivery rate of the polarized gaseous $^{129}$Xe into the injection site typically to about 1-3 cc/s or less for venous entry. The gas injection may be performed in a manner which reduces the bubble size associated with the injected gas to preferably to less than about 5-10 μm in diameter for certain embodiments (particularly for arterial injections) and less than about 75-150 μm in diameter for venous injections.

In one embodiment, a second quantity of a polarized gas is introduced to a subject during the same imaging session. That is, the first quantity is injected and an associated first image or signal acquisition can be obtained, and a second delivery and a second data or signal acquisition or image associated with the second quantity can be obtained. For example, the second delivery can be via inhalation of a hyperpolarized gas (either $^3$He or $^{129}$Xe, although for system equipment and coil tuning reasons, $^{129}$Xe gas is preferred) and the signal/image can be obtained after a short lapsed time period from the first signal/image (a time sufficient to clear traces of the polarized injected xenon from the target area). Additionally, or alternatively, the inhalation dose can be delivered prior to the injection of the polarized gas. Alternatively, concurrent delivery of the injection and inhalation doses may be used. It is anticipated that this may help with co-registration between the two images and may reduce image artifacts. Of course, the second delivery can be another injectable dose of $^{129}$Xe gas, or an injection of a hyperpolarized gas product in liquid form (such as dissolved in a carrier liquid).

Another aspect of the present invention is directed toward a method of obtaining MRI-based medical images. The method includes injecting directly into an injection site of a subject a first quantity of polarized $^{129}$Xe in gaseous form and delivering a second quantity of polarized gas product to the subject within the same imaging session. The second delivery can be performed in a number of ways and with a number of polarized noble gas product formulations. For example, inhalation of a polarized noble gas mixture (such as described for the embodiment above) or another injection (either of the $^{129}$Xe gas directly or of a polarized noble gas product otherwise formulated such as in a carrier or liquid based injection formulation) at a point in time which is proximate to the injecting step. The second quantity is larger than the first (injected) quantity. An MRI image is then generated corresponding to the signal data acquisition obtained via NMR excitation of the first and second quantities of polarized gas introduced in said injecting and delivering steps.

In certain embodiments, the injecting step injection site is a site associated with the venous vasculature (such as a vein). In one embodiment, the delivering step is carried out by administering two separate polarized gas based doses. That is, the delivery step may be performed by injecting to second site in an artery and by inhaling a quantity of hyperpolarized gas. The second site or arterial injection quantity can be in fluid or gas formulation. Thus, the inhalation based delivering step introduces the polarized gas via inhalation and the inhaled gas is subsequently directed into pulmonary arterial vasculature via perfusion uptake.

In another embodiment, the NMR signal data associated with both the injecting and delivering steps is processed in a manner which distinguishes NMR signal information corresponding to gas versus dissolved gas signal information in the MRI image generating step. Alternatively, the MRI image-generating step is performed at a low magnetic field strength, and the NMR signal data is processed in a manner which combines or does not substantially distinguish between NMR signal data associated with excitation of the hyperpolarized gas whether in the gas phase or the dissolved phase (the peaks associated with the polarized gas in the red blood cells and plasma in the blood overlap).

An additional aspect of the present invention is directed to a method of obtaining diagnostic images of the cranial region. The method includes the steps of injecting less than about 5 cc's (preferably about 1-2 cc's) of $^{129}$Xe polarized gas into an injection site in a carotid artery and dissolving the polarized $^{129}$Xe gas into the vasculature proximate to the injection site. An NMR image is generated having signal intensity associated with the NMR excitation of the dissolved $^{129}$Xe. The signal can be associated with the $^{129}$Xe in one or more of the blood, grey matter, CSP, or white matter (to provide information corresponding to white matter perfusion typical of desired neurological assessments). The excitation or response signal can be processed in a manner which allows the correlation to a particular region of interest, such as, for example, highlighting differences in chemical shift, $T_2^*$, $T_1$, and the like as will be appreciated by one of skill in the art. The method can include, inter alia, the step of introducing, in vivo, a surfactant to facilitate bubble dissipation proximate to the injection site In one embodiment, the injecting step is performed at a (controlled) rate and/or pressure sufficient to facilitate the dissolution of the gas in the vasculature proximate to the injection site and/or in a manner which reduces the size of bubbles introduced therewith corresponding to the selected injection site (preferably to form smaller size bubbles and smaller quantities of gas for arterial injections). An injection head with multiple orifices sized with a diameter of between about 1 nm-50 μm, and typically between about 0.01-10 μm can be used and the gas may be mixed in situ with an emulsifier prior to delivery to facilitate a fine dispersion of gas into the body of the subject.

Another aspect of the present invention is directed toward a method of obtaining an MR image or NMR spectral data. The method includes injecting less than about 100 cc's of hyperpolarized gas in vivo into an injection site associated with the vasculature of a mammalian subject. An NMR image or spectral data is then generated corresponding to the injected quantity of hyperpolarized $^{129}$Xe gas.

In one embodiment the method includes the step of administering the injection such that it remains substantially undissolved within the bloodstream for a period of time and such that it exhibits a $T_1$ in the bloodstream of at least eight seconds. Alternatively, the method can administer the injection such that is employs an introduction rate selected so that the gas is dissolved (at least partially) into the vasculature proximate to the injection site and/or to reduce the size of bubbles associated with the injection.

In certain embodiments, the injection is performed by injecting the hyperpolarized $^{129}$Xe into at least one predetermined injection site such as in an arm, leg, or at other externally accessible or viable injection locations. For example, the injection site can be chosen from the group consisting of a carotid artery, a pulmonary artery, a renal artery, a hepatic artery, and a renal artery or the group consisting of a vein located in the arm (such as the central vein or peripheral vein), a jugular vein, a pulmonary vein, a hepatic vein, and a renal vein. In another preferred embodiment, the injecting step is performed by injecting the hyperpolarized $^{129}$Xe into at least two different injection sites, preferably the injection sites corresponding to a vein or artery which is externally accessible via injection of an IV or syringe needle such as in an arm, leg, or at other torso or other feasible locations.

The injection dose can be contained in a single-dose sized container. For arterial injections, the dose container can be sized and configured to hold less than about 14-20 cc's of polarized $^{129}$Xe gas therein. For venous injections, the dose container can be sized and configured to hold less than about 100 cc's of polarized $^{129}$Xe gas therein. The container can be a syringe configured with a primary body with a wall having outer and inner surfaces, and the inner surface is formed from a material which reduces contact induced polarization decay associated therewith. Preferably, the syringe body is operably associated with a capillary stem and valve to control the exit of gas from the syringe. The syringe body can also include an NMR excitation coil mounted thereon. For delivery, it is preferred that a catheter is positioned in a subject at the desired injection site (corresponding to the desired target image region in the subject). The catheter can include or be operably associated with a frit or needle which is formed or coated with a polarization friendly material (such as a gold plated or aluminum needle). The frit or needle may also be configured and sized to reduce the bubble size to at or below about a 10 micron diameter at injection. This reduced bubble size may be particularly suitable for arterial injection sites.

In certain embodiments, an injection system for administering polarized gas to a subject can include (a) a polarized noble gas supply; (b) a catheter configured and sized for intravenous or intrarterial placement in a subject in fluid communication with the supply of polarized noble gas; and (c) an injection head positioned in a distal portion of the catheter. The injection head can comprise multiple orifices which are configured so that, in operation, hyperpolarized gas flows therethrough and out of the catheter into the subject. The orifices can be sized with a width which is between about 1 nm-50 μm, and typically between about 0.01-10 μm.

In certain embodiments, the system can include an additive source (such as an emulsifier source) and a mixing chamber positioned intermediate the orifices and the additive or emulsifier and polarized gas sources to mix the hyperpolarized gas and the additive or emulsifier prior to expulsion from the injector head orifices (typically it is mixed in situ as the gas flows away from the gas source toward the exit orifice(s) in the injection head). The system may also include a heating or cooling means to promote the generation of a fine dispersion of gas mixture from the injection head (which typically resides in an TV inserted into the body).

In preparing the syringe, catheter, injection system, and/or conduit associated therewith for use according to the present invention, $CO_2$ can be employed as a purge gas to prepare the container and reduce the likelihood of introducing nitrogen via injection into a subject (potentially leaving residual or traces of $CO_2$ rather than nitrogen which has been conventionally used to prepare the polarized gas containers). As such, the injectable $^{129}$Xe may include small quantities or traces of $CO_2$ therewith.

The system may include a resilient dose bag having external walls which are responsive to the application of pressure thereagainst and a quantity of hyperpolarized gas held in the dose bag along with an inflatable bladder which is sized and configured to receive at least a portion of the dose bag therein. In operation, the inflatable bladder is inflated to press against the dose bag external walls to thereby expel a quantity of the hyperpolarized gas from the dose bag.

In one embodiment, the present invention is configured to employ a dual path hyperpolarized gas product delivery system. For a manual presentation and delivery, a technician can deliver the $^{129}$Xe (inject) and then trigger a switch in the MRI unit indicating that the delivery is complete. The MRI unit, in response to activation of the switch, can initiate the imaging procedure such that it commences within the required polarization life at the target-imaging region. The MRI unit can also have a timer operably associated therewith which can alert the technician when it is acceptable to deliver the inhalation dose. The inhalation dose can be an optional delivery which is withheld if no reasonable indicia of perfusion deficits are indicated by NMR signal obtained based on the injected dose. Of course, the injection dose and the inhalation dose order can be reversed, wherein the injection dose is administered second. In addition, automated delivery and sequencing methods can also be employed as will be appreciated by one of skill in the art.

For concurrent delivery, the system can include a user audible and/or visual alert which is responsive to one or more of the dispensing systems (it is activated when a gas or liquid polarized product commences delivery at an IV or inhalation or other administration) that allows the dispensing of more than one dose/path of gas (such as the inhaled and injected gas) to be timed or substantially concurrently (or at a predetermined or desired interval) administered. This can facilitate the effective delivery and initiation of imaging sequences which can be important due to the limited polarization life of the polarized gas product in the blood.

An additional aspect of the present invention is a method of evaluating the efficacy of targeted drug therapy, comprising the steps of delivering a quantity of a predetermined gene treatment preparation or pharmaceutical drug in vivo into a mammalian subject having a target site and a treatment condition; injecting a predetermined quantity of gaseous phase hyperpolarized $^{129}$Xe in vivo into a mammalian subject such that the hyperpolarized gas is delivered to the target site in gaseous or dissolved form; generating a NMR image or spectroscopic signal of the target site associated with the injected hyperpolarized $^{129}$Xe gas; and evaluating the NMR image or spectroscopic signal to evaluate the efficacy of the gene treatment or drug on the treatment condition administered in the delivering step.

In one embodiment, the method further comprises the step of acquiring at least two sets of data, the data representing two temporally spaced apart points in time, to evaluate if the treatment condition is influenced by the drug or gene therapy introduced in the delivering step. Of course, the evaluation may be performed without regard to toxicity and/or survival if done in connection with animal research.

Another aspect of the invention is a method of determining the presence of cancerous tissue, comprising the steps of delivering a quantity of a pharmaceutical drug in vivo into a mammalian subject having a target site associated with a suspect mass or tissue abnormality; injecting a quantity of gaseous hyperpolarized $^{129}$Xe in vivo into a mammalian subject such that the hyperpolarized gas is delivered to the target site; generating a NMR image or spectroscopic signal of the target site corresponding to the injected hyperpolarized $^{129}$Xe gas; and evaluating the NMR image or signal for the presence or absence of signature patterns in the generated image or signal associated with the presence or absence of cancer.

An additional aspect of the present invention is an injectable $^{129}$Xe gas product, the $^{129}$Xe gas product formulated as a sterile non-toxic hyperpolarized gas formulation which consists essentially of isotopically enriched $^{129}$Xe in gaseous phase which is injected in vivo in a quantity of less than about 20-100 cubic centimeters.

Similarly, another aspect of the present invention is an injectable $^{129}$Xe gas pharmaceutical grade product, the product formulated as a sterile non-toxic product which consists essentially of $^{129}$Xe in gaseous phase and traces of $CO_2$, wherein the injectable gas product is configured to be dispensed in vivo.

The present invention is advantageous because relatively small quantities of (preferably isotopically enriched) hyperpolarized $^{129}$Xe gas with relatively predictable or known polarization levels can provide high-quality MRI images or spectroscopy data with clinically useful signal resolution for in vivo tissue and/or vasculature. Indeed, in one preferred embodiment, the pulmonary embolism detection method can be performed as a relatively quick screening method typically with high quality diagnostic information about the circulatory path, such as in under about 15 minutes. In this embodiment, it is preferred that both an inhalation (ventilation) and injection delivery of hyperpolarized gas are used to generate a combined (dual) introduction path. That is, inhalation can provide a first order image or ventilation image of the lungs. However, the gas migrates into the vasculature and/or is uptaken by the blood stream and, thus, is introduced into a pulmonary vein(s). This uptake can provide MRI or NMR venous spectra/information of the venous side of the circulatory system. In contrast, the injection into a venous pathway can yield NMR arterial signal information (generally described, the $^{129}$Xe gas injected in a vein travels/flows to the right side of the heart and then into a pulmonary artery). Therefore, the dual introduction path can provide a more complete image/signal of both the arterial and venous side of the pulmonary vasculature. Conveniently, by using polarized $^{129}$Xe gas both as the inhalation and injection NMR medium, the pulmonary embolism screening method can use the same NMR chest coil for the excitation and detection of the $^{129}$Xe signals associated with the inhaled/perfusion dose and the injected dose.

Of course, direct injection of $^{129}$Xe polarized gas to a particular target site such as a tumor can allow for additional diagnostic information over many conventional procedures. For example, in vivo cancerous tumors can be characterized by the presence of increased random blood vessel growth (a condition known as angiogenisis). This is in contrast to benign cysts. Taking advantage of this characteristic and the NMR signal information available using direct $^{129}$Xe polarized gas injection, the present invention can analyze in vivo a target in an organ such as a tumor in a breast. For example, a needle can be inserted or injected to the suspect region in the breast via conventional MR guided needle placement and $^{129}$Xe can be released thereat (along with or in lieu of removing biopsy materials). Signature peaks in spectroscopy signals (or improved image resolution attributed to the hyperpolarized $^{129}$Xe signal) can indicate the presence of cancer via the increased peak in the signal due to the increased blood (and the injected xenon's solubility therewith). Of course, other contrast mechanisms like chemical shift, $T_2$*, diffusion, $T_1$, and the like, can also be employed to exploit the $^{129}$Xe NMR image or spectroscopic signal in the tumor.

In addition, the present invention preferably employs a reliable quantitative concentration and/or predictable injection quantity. This predictable concentration of polarized gas can provide more predictable and reliable signal intensity for the associated MRI image, which, in turn, makes the method clinically useful as well as easier to correlate, patient to patient, or in a single patient over time. Preferably, the injectable quantity is selected to correspond to the introduction (injection) site; the venous side can use increased quantities compared to the arterial side (the venous side injections preferably sized at about 100 cc's or less while the arterial injections are typically sized at about 14-20 cc's or less.

In addition, the gas is preferably injected in a manner which facilitates reduced size bubbles introduced or formed by the injecting of gas. Controlling one or more of bubble size based on its responsive parameters, the quantity of gas administered, and/or injection rate (release) (as well as the configuration of the nozzle or exit chamber) of the gas can assure that the gaseous delivery to vasculature is done in an effective manner.

In one embodiment, the in vivo introduction of a suitable surfactant temporally and spatially proximate to (preferably upstream) the actual injection of the gas (temporally before or concurrent to the gas injection) can facilitate the dissipation or decreased size of injected bubbles in the venous and/or arterial system (depending on the injection site).

Further, the present invention recognizes that in order to allow the injected xenon gas sufficient time to enter the pulmonary vasculature, the NMR scanning is preferably delayed a sufficient amount of time after injection to allow for same, typically about 5-10 seconds post-injection. On the upper time limit, the NMR scan is also preferably performed within about one minute post-injection (and preferably 30 seconds after injection) as the polarization level will decay to an undesirable level relatively shortly after introduction into the body. Of course, multiple serially successive quantities of administered injection doses can be administered during the imaging session for obtaining a plurality of sequential or multi-shot images.

The dispensing methods, containers, and other apparatus of the present invention are advantageously configured to facilitate a longer $T_1$ for the polarized gas and, thus, to promote a single-bolus sized formulation with a predictable level of polarization in a hyperpolarized product. Further, the $^{129}$Xe injectable gas product can be delivered and formulated in a way which allows the gas to be analyzed to determine its polarization level prior to delivery to thereby confirm the efficacy of the product just prior to (or in a preferred temporally appropriate point prior to) introduction into the patient.

Further, the present invention provides methods for sizing the length of a capillary stem on a container having a primary hyperpolarized gas holding chamber with a volume, the capillary stem having a volume which is substantially less than that of the gas holding chamber and includes a wall defining a flow channel aperture having a radius or width and a length. The wall has a gas-contacting surface formed of a material having a relaxivity value for a selected hyperpolarized gas associated therewith. The method comprises the steps of defining a capillary stem aperture size; establishing a relaxivity value for the material forming the capillary wall; and calculating an optimal capillary stem length. Similarly, the present invention can configure containers with capillary lengths chosen to increase the polarized life of the gas held therein.

BRIEF DESCRIPTION OF THE DRAWINGS

FIGS. 8A and 8B are perspective views of yet another alternative gas delivery system according to the present invention. FIG. 8A illustrates the gas container with an inflatable inner membrane member. FIG. 8B illustrates the inner membrane member expanded to expel or force a quantity of hyperpolarized gas out of the chamber. FIG. 8B also illustrates a NMR monitor coil positioned to detect the polarization level of the gas, preferably just prior to dispensing into the subject.

FIG. 8C is an enlarged end view of the exit surface of an injector head according to embodiments of the present invention.

FIG. 8D is a schematic drawing of an injection system according to embodiments of the present invention.

FIG. 8E is a schematic drawing of an alternative injection system according to embodiments of the present invention.

FIG. 8F is an enlarged sectional view illustrating at least two separate flow channels and a mixing chamber upstream of gas outlet ports according to embodiments of the present invention.

FIG. 8G is a greatly enlarged partial side view of an injection head having a convergent nozzle configuration according to embodiments of the present invention.

FIG. 8H is a greatly enlarged partial sectional side view of an end portion of an injection head according to embodiments of the present invention.

FIG. 8I is a greatly enlarged partial sectional side view of an alternate configuration of an end portion of an injection head according to embodiments of the present invention.

DETAILED DESCRIPTION OF PREFERRED EMBODIMENTS OF THE INVENTION

Figure 1A:
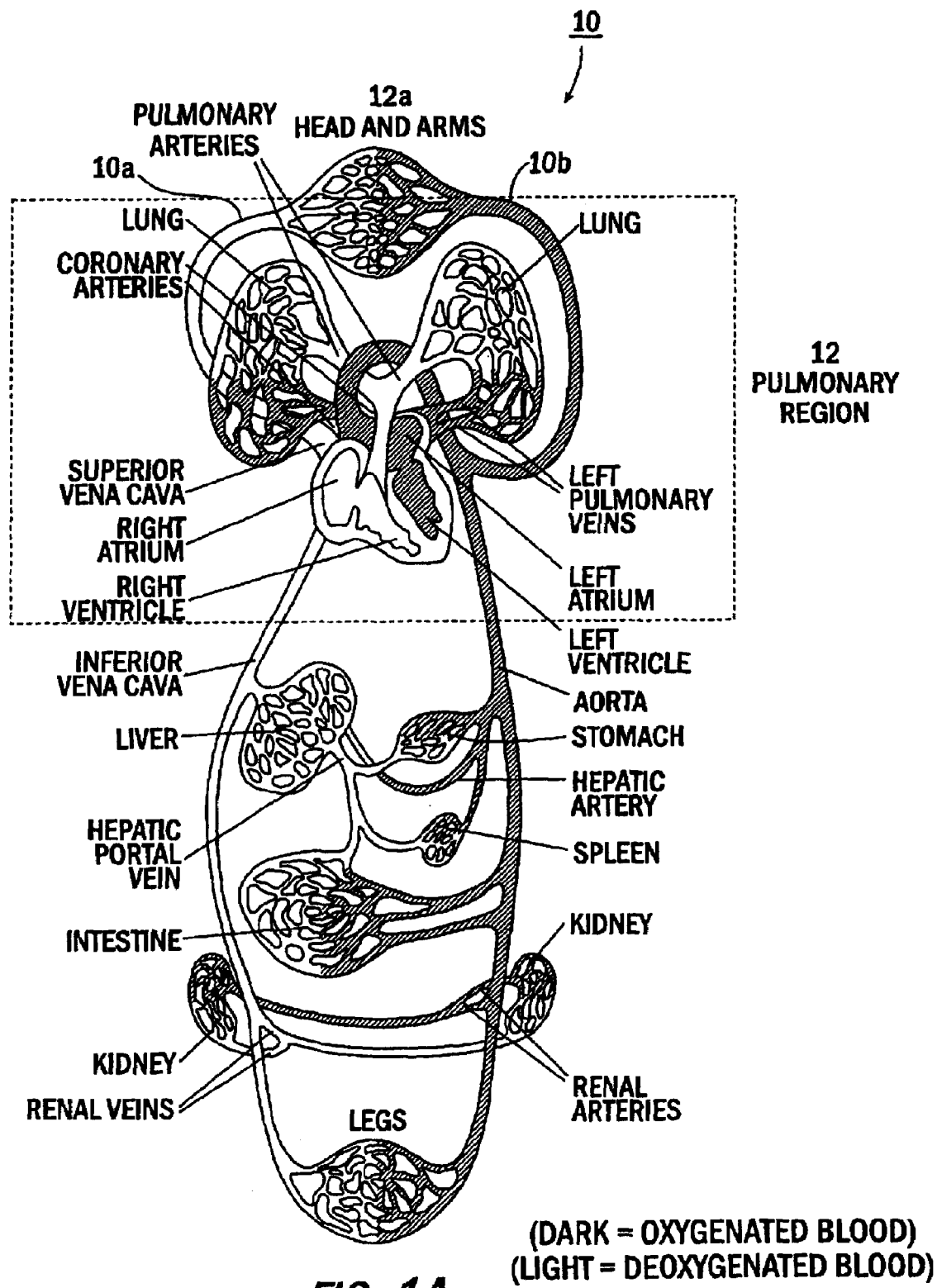
FIG. 1A is a schematic illustration of the human circulatory system illustrating the venous and arterial portions thereof. The deoxygenated blood is represented by the lighter/white regions and the oxygenated blood is represented by the darkened regions.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. In the figures, certain layers, regions, or components may be exaggerated or enlarged for clarity.

As known to those of skill in the art, polarized gases are collected, frozen, thawed, and used in MRI applications. For ease of description, the term "frozen polarized gas" means that the polarized gas has been frozen into a solid state. The term "liquid polarized gas" means that the polarized gas has been or is being liquefied into a liquid state. The term "gaseous" hyperpolarized $^{129}$Xe indicates the gaseous phase of the "hyperpolarized $^{129}$Xe gas". Thus, although each term includes the word "gas", this word is used to name and descriptively track the gas which is produced via a hyperpolarizer to obtain a polarized "gas" product. Thus, as used herein, the term "gas" has been used in certain places to descriptively indicate a hyperpolarized noble gas product and may be used with modifiers such as solid, frozen, and liquid to describe the state or phase of that product.

Various techniques have been employed to accumulate and capture polarized gases. For example, U.S. Pat. No. 5,642,625 to Cates et al., describes a high volume hyperpolarizer for spin polarized noble gas and U.S. Pat. No. 5,809,801 to Cates et al. describes a cryogenic accumulator for spin-polarized $^{129}$Xe. U.S. Pat. No. 6,079,213 to Driehuys et al., entitled "Methods of Collecting, Thawing, and Extending the Useful Life of Polarized Gases and Associated Apparatus," describes an improved accumulator, collection and thaw methods, and xenon gas heating means. The disclosures of these documents are hereby incorporated by reference as if recited in full herein.

As used herein, the terms "hyperpolarize", "polarize", and the like, mean to artificially enhance the polarization of certain noble gas nuclei over the natural or equilibrium levels. Such an increase is desirable because it allows stronger imaging signals corresponding to better MRI (and spectroscopy) images of the substance and a targeted area of the body. As is known by those of skill in the art, hyperpolarization can be induced by spin-exchange with an optically pumped alkali-metal vapor or alternatively by metastability exchange. See Albert et al., U.S. Pat. No. 5,545,396. Other methods may also be used, such as dynamic nuclear polarization ("DNP") and "brute force" methods which propose to cool the $^3$He or $^{129}$Xe to very low temperatures and then expose them to very high magnetic fields to enhance the thermal equilibrium polarization.

Generally stated, the present invention recognizes that direct gaseous injection of hyperpolarized $^{129}$Xe can be a viable, safe, and effective delivery method when the gas is formulated and delivered in a manner which reduces the potential for formation of emboli within the vasculature. Unlike many previous injectable formulations, the present invention employs a gaseous formulation of inert polarized (preferably "isotopically enriched" polarized $^{129}$Xe gas as will be discussed further below) $^{129}$Xe which is packaged in a polarization friendly (increased longer relaxation life) container or syringe to provide an injectable pharmaceutical grade gas phase product. The gas phase injectable formulated hyperpolarized $^{129}$Xe can be an effective image enhancing product when delivered at a controlled rate and/or quantity with a predictable polarization level which can provide improved image resolution and/or diagnostic capability without the need for additional liquid carrier agents and mixing. Direct gaseous injection has many advantages that can not only simplify the diagnostic procedure, it can also restore the sensitivity of $^{129}$Xe to its environment and can improve the delivery efficiency of polarized $^{129}$Xe to target tissues. The gaseous injection can be performed such that it remains substantially non-dissolved in the bloodstream over about 8-10 seconds from the time of injection, or can be performed such that it is at least partially, and even substantially, dissolved proximate to the injection site or within a short period from the time of injection (i.e., less than about 2-4 seconds).

Further, in certain embodiments the gaseous formulation can eliminate the use of an external fluid-mixing step. Still further, the hyperpolarized $^{129}$Xe can be contained in a specialized gas syringe with increased relaxation times as will be discussed further below. In certain embodiments, the degree of polarization is measured via an NMR coil located on the dispensing container itself which can be utilized just prior to administration. Thus, the NMR signal strength can be more accurately/reliably correlated to the polarization level and also the administration can be performed in a relatively calm, relaxed manner, without the impending threat and constraints of rapid decay elicit in many conventional short $T_1$ formulations.

Referring now to FIG. 1A, a human circulatory system 10 is schematically illustrated. The oxygenated blood within the vasculature is represented by the darker regions while the deoxygenated blood is represented by the white or lighter regions.

Figure 3A:
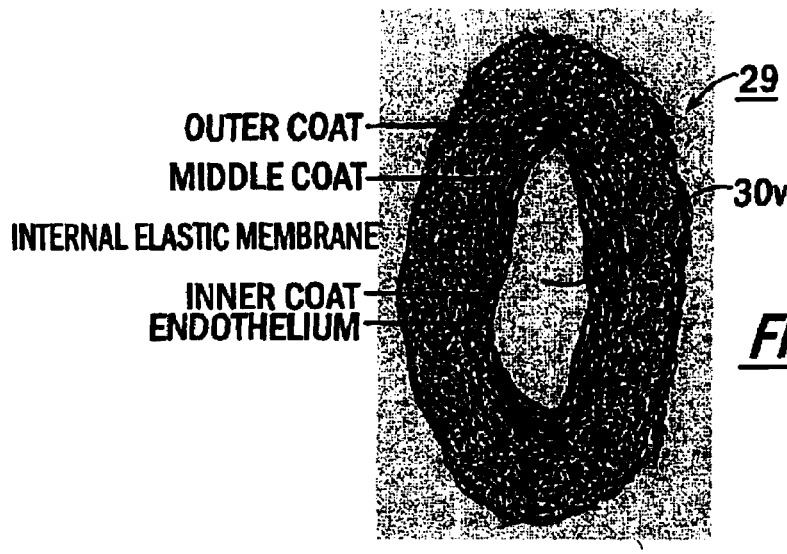
FIG. 3A is a cross-sectional view of a vein.
Figure 3B:
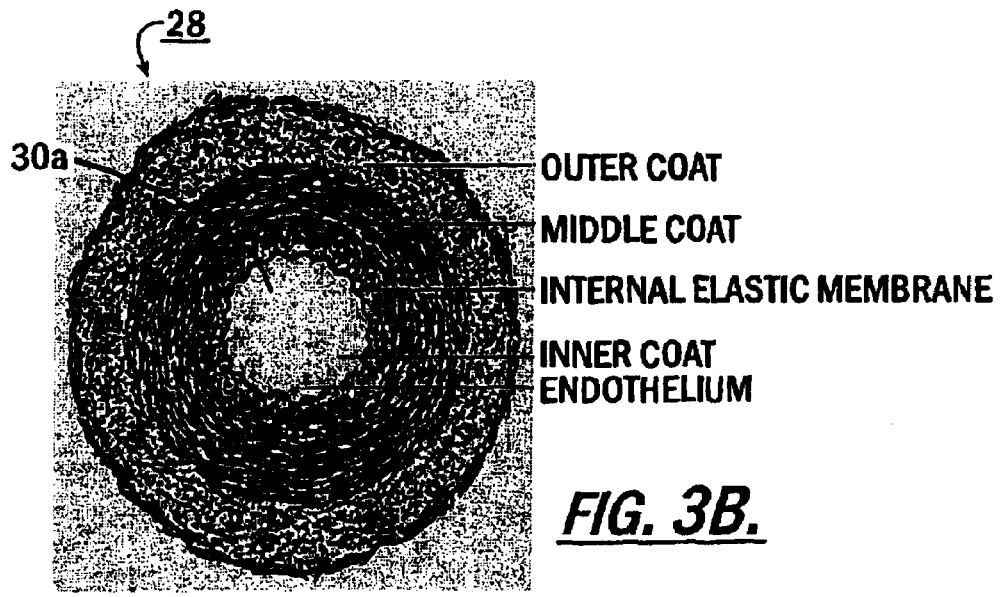
FIG. 3B is a cross-sectional view of an artery.

As used herein the term "vasculature" includes boundary tissue, cells, membranes, and blood vessels such as capillaries, venules, veins, arteries, arterioles, and the like associated with the circulatory system and blood flow path and/or channels of blood. Typically, as shown in cross sectional views in FIGS. 3A and 3B, the artery flow channels 30a are smaller and more rigid and round compared to the vein flow channels 30v.

The gaseous $^{129}$Xe injection of the present invention has some similarities to a technique presently used, called digital subtraction (DSA) $CO_2$ angiography. Generally described, in this conventional procedure, $CO_2$ is rapidly injected to displace a portion of the blood. An X-ray image is taken quickly after injection. Where the $CO_2$ has displaced the blood, there is reduced X-ray opacity and the image appears brighter. Typically, a second X-ray is taken without $CO_2$ injection and the two images are digitally subtracted to show the contrast. $CO_2$ DSA is used instead of traditional iodinated contrast agents because of the "nephrotoxicity" of iodine-based contrast agents. The volumes of $CO_2$ injected range from roughly 10 cc's to 50 cc's (the larger quantity for larger blood vessels). In addition, the injection rate is quite rapid (10 ml/s to 100 ml/sec) inasmuch as contrast only results from the displacement of blood. Generally stated, after injection, $CO_2$ is efficiently dissolved into the blood and exhaled upon passage through the pulmonary capillary bed. Stated differently, $CO_2$ exits the blood into the lung alveoli via diffusion through pulmonary capillary. A review of this technique has been presented by Hawkins and co-workers. Kerns et al., *Carbon Dioxide Digital Subtraction Angiography: Expanding Applications and Technical Evolution,* 164 Am. Jnl. Radiology, pp. 735-741 (1995).

The feasibility of gaseous $^{129}$Xe injection, particularly for arterial injections, may appear problematic. For example, it is known that arterial injections of air can lead to an undesirable air embolus. Although with intravenous (IV) injection the introduction of air is less of a concern, great care is typically taken to avoid such occurrences. The injection of $CO_2$ is successful because of its high solubility in blood and the body's unique ability to remove it. The solubility of $CO_2$ in blood and plasma can be difficult to measure because it is chemically metabolized. However, its solubility in water is 0.63 and it has been measured in RBC (red blood cell) ghosts to be about 1.0. Table 1 below shows the solubilities of other relevant gases in water plasma and blood.

TABLE 1

Solubilities of Gases

| Gas | Water | Plasma | Blood | Other |
|---|---|---|---|---|
| He | 0.0098 | 0.0086 | 0.0094 | 0.0105 (lung) |
| $N_2$ | 0.0143 | 0.0134 | 0.0148 | 0.109 (RBC ghosts) |
| $O_2$ | 0.0271 | 0.0243 | 0.0261 | 0.13 (RBC ghosts) |
| $CO_2$ | 0.631 | — | — | 1.0 (RBC ghosts) |
| Xe | 0.089 | 0.105 | 0.167 | 0.181 (liver) |

As $CO_2$ in plasma and blood are metabolized before the measurements can be obtained, no numbers are listed for these entries in Table 1. Nonetheless, it is believed that the solubility that is of primary interest for the discussion herein and that the $CO_2$ metabolism can be disregarded for the purposes of this comparison.

Table 2 below shows the solubilities of these gases relative to $CO_2$ (i.e., the relative solubility "$S_r$" is represented by the ratio of:

(Solubility of named gas in water)/(Solubility of $CO_2$ in water).

TABLE 2

| Gas | Sr (relative) |
|---|---|
| $CO_2$ | 1 |
| Xe | 0.14 |
| $O_2$ | 0.043 |
| $N_2$ | 0.023 |
| He | 0.016 |

Relative Solubility ($S_r$)

Table 2 illustrates the higher solubility of xenon compared to the major constituents of air ($O_2$ and $N_2$) but also shows that $CO_2$ is considerably more soluble than xenon. Therefore, the present invention recognizes that direct gaseous injection of polarized $^{129}Xe$ can be a useful in vivo diagnostic NMR imaging tool and also recognizes that proper sizing of the injectable quantities and/or the injection rates are important considerations for achieving same. Accordingly, the present invention provides a maximum preferred arterial xenon injection volume by comparing the solubilities of xenon and $CO_2$. Maximum $CO_2$ injection volumes are typically limited to about 50-100 cc's of gas. By taking the relative solubilities above into consideration, the maximum xenon injections can be predicted to be about 0.14 times the quantity or volumes of $CO_2$. Thus, particularly for arterial injection sites, for a $CO_2$ volume of 100 cc's, the xenon injection volume is preferably limited to about 14-20 cc's. For the smaller range of injected $CO_2$, such as a 10 cc injection volume, a 1.4-2.0 cc volume of polarized $^{129}Xe$ gas is preferably dispensed according to the present invention.

In contrast, for non-arterial sites, such as for venous injection sites, a larger injection quantity may be tolerated. That is, it is known that the introduction of air into venous sites which is on the order of 300-400 cc's can be particularly troublesome and even potentially fatal. Xenon, although less soluble in blood than $CO_2$, is about 10 times more soluble than air (i.e., it can dissolve faster in blood than air). Thus, even with a safety factor, the venous site injections can be typically sized at quantities in the range of about 100 cc's, although preferably sized at less than 100 cc's. Of course, such injection volumes also depend on the vessel type and size being injected into.

Along with the quantity of the gas formulated for injection, the generated bubble size and/or bubble dissipation can be important considerations for in vivo applications, particularly for arterial injection sites. In certain embodiments, a surfactant can be injected proximate in time and location to the gas injection site to either help dissipate the size of the bubble and/or to lower the blood surface tension. Surfactants have been studied by van Blankenstein et al. to aid in the recovery from venous air embolism. See J. H. van Blankenstein et al., *Cardiac Depression after Experimental Air Embolism in Pigs: Role of Addition of a Surface-Active Agent,* 34 Cardiovascular Research, pp. 473-482 (1997). In this study, air bubbles with a diameter of about 150 µm were injected into the left anterior descending coronary artery in the presence or absence of antifoam. A 1:250 dilution of silicone antifoam 1510 EU (from Dow Corning) in pure water was used. The study indicates that the in vivo introduction of surfactants can reduce bubble dissipation time in blood.

It is contemplated by certain embodiments of the present invention that any suitable in vivo physiological compatible or acceptable surfactant can be employed whether of natural (human or bovine) or synthetic origin, and/or combinations thereof. Suitable physiologically acceptable formulations are known to those of skill in the art. See e.g., U.S. Pat. No. 4,826,821 to Clements, U.S. Pat. No. 4,312,860 to Clements, and U.S. Pat. No. 5,309,903 to Long (all discussing the use of surfactants in vivo for respiratory distress syndrome). These disclosures are hereby incorporated by reference as if recited in full herein. See also Horbar et al., *A Multicenter Randomized, Placebo-controlled Trial of Surfactant Therapy for Respiratory Distress Syndrome,* 320 The New England Jnl. of Med., No. 15, pp. 959-965 (Apr. 13, 1989) (discussing organic solvent extract of cow-lung fortified with dipalmitoylphosphatidlydhloine known as "SURVANTA" from Abbott Laboratories in Chicago, Ill.). Preferably, the surfactant is also chosen such that it is substantially non-depolarizing to the hyperpolarized state of the gas. The surfactant may be delivered via injection or insertion into the body proximate to the target gas injection site such that it facilitates bubble dissipation or reduces blood surface tension while also being substantially non-depolarizing to the polarized state of the gas (to help reduce the formation of emboli attributed to the injected gas).

As briefly discussed above, the injection of the gas can be carried out in a manner which reduces or limits the bubble size associated therewith. To better understand bubble dissipation, one can model a string of contiguous bubbles as a cylinder to look at the diffusion of the gas out of the "cylinder" into the surrounding fluid to analyze how the bubble volume or radius decreases with time. Presser et al., in modeling a simulation as stated above, noted that the bubble radius "r" versus time can be represented by the equation:

$$dr/dt = -K\Delta P/[r\ln(R/r)]$$

where "K" is Krogh's coefficient (the product of solubility "S" and diffusion coefficient "D" of the gas in the surrounding fluid), "$\Delta P$" is the pressure difference between gas in the bubbles and gas in the alveoli and "R" is the distance from the center of the bubbles to the inner edge of the adjacent alveoli. See Presser et al., *Fate of Air Emboli in the Pulmonary Circulation,* 67 J. Appl. Physiol. 5, pp. 1898-1902 (1989). To solve the equation requires numerical techniques, but the relationship can be generally characterized as being substantially linear for air down to about a 10 µm radius bubble, at which size the rate of dissipation is increased (i.e., it becomes steeper and more exponential-like). Presser et al. also notes that for air bubbles with radius' greater than about 10 µm, $dr/dt=-0.132$ µm/s. Thus, generally speaking, a 30 µm radius air bubble takes about 230 seconds to dissipate.

In contrast, as recognized by the instant invention, xenon bubble dissipation occurs at a faster rate than air. That is, for comparative analysis, it is believed that one can evaluate the Krogh's coefficient (S×D) for Xe relative to air. The diffusion coefficient is substantially the same and can be cancelled out. For example, Xe in $H_2O$ is about $1.9 \times 10^{-5}$ $cm^2/s$ while methane and water itself are at 2 and $2.3 \times 10^{-5}$ $cm^2/s$, respectively. Thus, solubility "S" becomes the important factor. Therefore, approximating air as nitrogen, the solubility ratio of xenon gas to nitrogen gas in blood is (0.167/0.0148), or about eleven (11). Accordingly, the bubble dissipation rate (dr/dt) for xenon is estimated at −1.5 μm/s. The same 30 μm radius bubble will dissipate in about 20 seconds. This additionally supports the direct injectability of $^{129}$Xe polarized gas into systemic arterial and venous circulatory injection sites.

Air bubbles of various sizes have been produced for injection into a coronary artery. See Van Blankenstein et al., *Heart Function after Injection of Small Air Bubbles in Coronary Artery of Pigs*, 67 J. App. Physiol. 5, pp. 1898-1902 (1989). In this study, air bubbles of 75, 150, and 300 μm diameter were formed with tolerances of about 10 μm. Generally stated, a micropipette with a constant-pressure source of air was used to form the desired bubble size. Factors impacting the formation of bubble size were pipette diameter, air (gas) pressure, and the flow of fluid through the pipette (flow volume in the artery may also be parameter to be considered). It is anticipated that calibration curves can be generated based on these factors (i.e., bubble-size dependent variables) to generate the desired bubble size.

In any event, in certain embodiments, the hyperpolarized $^{129}$Xe gas can be directly injected into the subject, such as into the blood stream of the subject, in bubble-sizes in the range of between 1 nm to 300 μm, and preferably in the range of between about 0.5-10 μm.

In order to generate a series of sequential bubbles for injection, it is preferred that a frit or custom fabricated lumen (small diameter) configuration can be employed and/or with a controlled pressure set to form the desired bubble size (not shown). In certain embodiments, the frit may comprise glass (such as a substantially magnetically pure aluminosilicate or surface coated glass to reduce surface relaxation effects). A differently sized/configured frit (exit diameter/shape) or lumen may be formed for various injection sites (particularly to facilitate the production of smaller bubble size for arterial applications) and located such that it is in fluid communication with the conduit or even integrated into the syringe or IV or other catheter body itself.

In any event, a polarized $^{129}$Xe gas injection quantity of as low as under 5 cc's, such as just 1-2 or 1-3 cc's, but typically at least about 14-20 cc's (depending upon the injection site), can provide improved signal strengths even over larger amounts with conventional hyperpolarized inhalation techniques (although greater quantities can be used as discussed above). For example, the brain-imaging example described above shows that an injection of just 1, 2, or 3 cc's of $^{129}$Xe can result in larger signals than can be typically achieved through inhalation of 1 liter of hyperpolarized $^{129}$Xe. The signal strength can be improved to be even stronger if isotopically enriched polarized $^{129}$Xe is employed.

Furthermore, unlike injection of $CO_2$, the $^{129}$Xe injection does not have to be performed at a rate which is fast enough to displace the blood. The $^{129}$Xe can be readily imaged if it is (a) dissolved in the blood, or (b) if it remains (largely or in smaller amounts) in the gas phase as it travels in the bloodstream for imaging purposes.

In the case of an arterial injection where rapid dissolution of the xenon into the blood stream may be desired, the gas injection can be performed at a rate which is sufficiently slow so that the xenon can substantially dissolve into the blood stream as it is injected therein. Mathematically stated, this injection rate limit may be set at about $$\frac{d}{dt}V_{xe} = \lambda Q$$

where "λ" is the xenon solubility in blood and "Q" is the volumetric blood flow rate in the vessel being injected. Injection at this speed can result in substantially fully xenon-saturated blood in the injection region. In certain embodiments, the injection rate can be selected such that it is less than the blood flow rate within the injection site. The injection rate can be carried out such that it is less than about 25-50% of the blood flow rate, particularly for arterial injection sites. For example, blood flow in the hepatic artery in an average adult is roughly 5.8 cc/s, so it is anticipated that a xenon gas injection rate of about 1-5 cubic centimeter per second (cc/s), and in certain applications 2.9 cc/s or less, or in other applications about 1 cc/s or less should be physically tolerable and sufficiently rapid to deliver a quantity which can yield clinically acceptable NMR images and/or signals.

Figure 4:
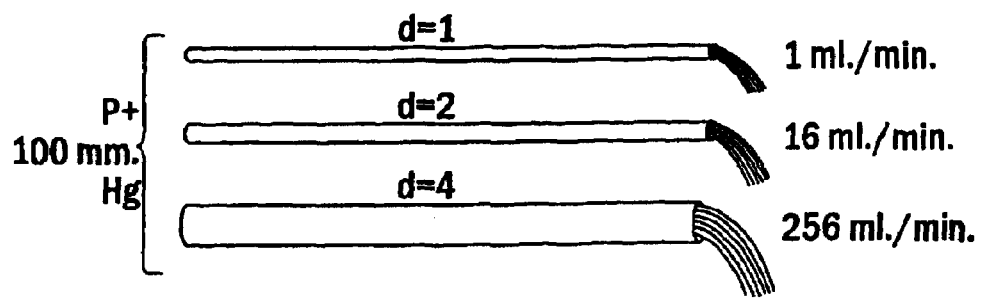
FIG. 4 is a side view of different sized blood vessels illustrating different flow rates corresponding to diameter of the vessel at a particular pressure.

FIG. 4 illustrates three different flow rates and associated vessel diameters (at flow rates smaller than the hepatic artery described above (5.8 cc/s=348 ml/min)). Of course, especially for more distal target imaging regions and/or smaller injection quantities, or where is desirable to retain a larger portion of the gas non-dissolved in the bloodstream, faster injection rates can be employed.

Venous injections using even larger xenon volumes or quantities and/or more rapid $^{129}$Xe injection rates (as well as larger bubble size) as compared to the arterial injection sites may also be suitable. For example, for 100 cc's of injectable gas, a suitable injection rate can be about 2-3 cubic centimeters per second. In other applications, rates substantially equal to or less than about 2 cc/s may be appropriate. The injection rates can be controlled in a number of ways such as via manual or automated (or semi-automated) operation as will be appreciated by those of skill in the art. See e.g., U.S. Pat. No. 3,623,474 to Heilman et al. and U.S. Pat. No. 5,322,511 to Armbrusther et al. (describing power injection equipment). The contents of these documents are hereby incorporated by reference as if recited in full herein.

In contrast to inhalation methods, the gas-injection method allows smaller amounts of hyperpolarized gas to be effectively administered in smaller clinically effective doses. This smaller dose gas-based administration also allows for a commercially advantageous use of isotopically enriched (typically more a expensive formulation) polarized $^{129}$Xe. "Isotopically enriched" means $^{129}$Xe which has been enriched over natural levels (the natural level is about 26%). Preferably, the $^{129}$Xe gas which is polarized is enriched to a level which is isotopically enriched to at least about 50%, and more preferably enriched to at least about 70%, and still more preferably enriched to at least about 80%.

The present invention now allows the arterial side of the pulmonary vessels to be directly imaged rather than inferring or predicting ventilation defects vicariously as proposed in conventional inhalation based systems. That is, as discussed above, injection into a vein, allows the polarized gas to travel in the bloodstream through the heart and then into the pulmonary artery. In contrast, inhalation allows ventilation-based images and then as the polarized gas travels into the bloodstream through the pulmonary vasculature, it travels into the pulmonary venous circulatory flow path and can allow signal information corresponding to the venous system.

Still further, the imaging techniques which employ direct injection of hyperpolarized gas can provide perfusion images which are unobscured by ventilation defects typically associated with conventional inhalation-based images. That is, the inhalation methods may show a perfusion defect where a ventilation defect resides, because gas may be blocked from entering the vessels. In contrast, direct gas injection methods of the present invention can show "real" perfusion defects, ie., defects attributed (solely) to perfusion blockage. In addition, as noted above, using both inhalation and injection delivery of polarized gas as described herein can provide complementary diagnostic information and detail.

It should also be noted that NMR imaging or signal acquisition of $^{129}$Xe in the gas phase in the blood can provide increased an increased $T_1$ over that of the gas dissolved in the blood. In addition, $^{129}$Xe dissolved into the blood may provide a broader spectrum attributed to the rapid exchange between the $^{129}$Xe in RBC's and plasma. Unfortunately, a broad spectral line typically translates to a relatively short $T_2^*$. Therefore, sizing and delivering the injectable dose so that it remains substantially as a gas in the bloodstream can allow longer data acquisition times and/or improved images or signals therefrom.

Of course, the injection rate or release rate (volume over time) can be selected such the polarized gas is solubilized (substantially dissolved) into the blood proximate to the injection site. Alternately, the injection rate can be selected such that the gas is only partially or insubstantially solubilized in the blood proximate to the injection site or such that it remains in a non-dissolved state for a longer period of time as it travels through the bloodstream. For example, introducing the hyperpolarized gas into a vein (through the walls of the vessel) such that it retains sufficient polarization to render a clinically useful gas-phase signal after about 8-10 seconds, and preferably after about 8-20 seconds, from the time of injection. Maintaining the hyperpolarized gas in the gas phase (such that it is not substantially dissolved into the bloodstream) can increase the $T_1$ of the gas in the body. This, in turn, can allow longer image acquisition times during which the signal can be picked up as a viable clinically useful diagnostic tool. Again, the venous injection sites can generally withstand a greater injection volume and/or a greater delivery rate than a similarly sized arterial vessel.

Indeed, in the past, about 1 ml of air in 10 ml of saline was injected into the right internal jugular (IJ) vein of a human and monitored with ultrasound for IJ valve competence. See Ratanakorn et al., Jn. Of Neuroimaging, Vol. 9, pp. 10-14 (1999). It is expected that about 1-10 ml of hyperpolarized $^{129}$Xe gas, preferably configured with reduced bubble sizes (preferably at about or less than 10 microns) injected into the IJ will also yield clinically useful images and/or spectra (the hyperpolarized xenon gas bubble dissipation being about 11 times faster than air in blood as discussed above).

Figure 1B:
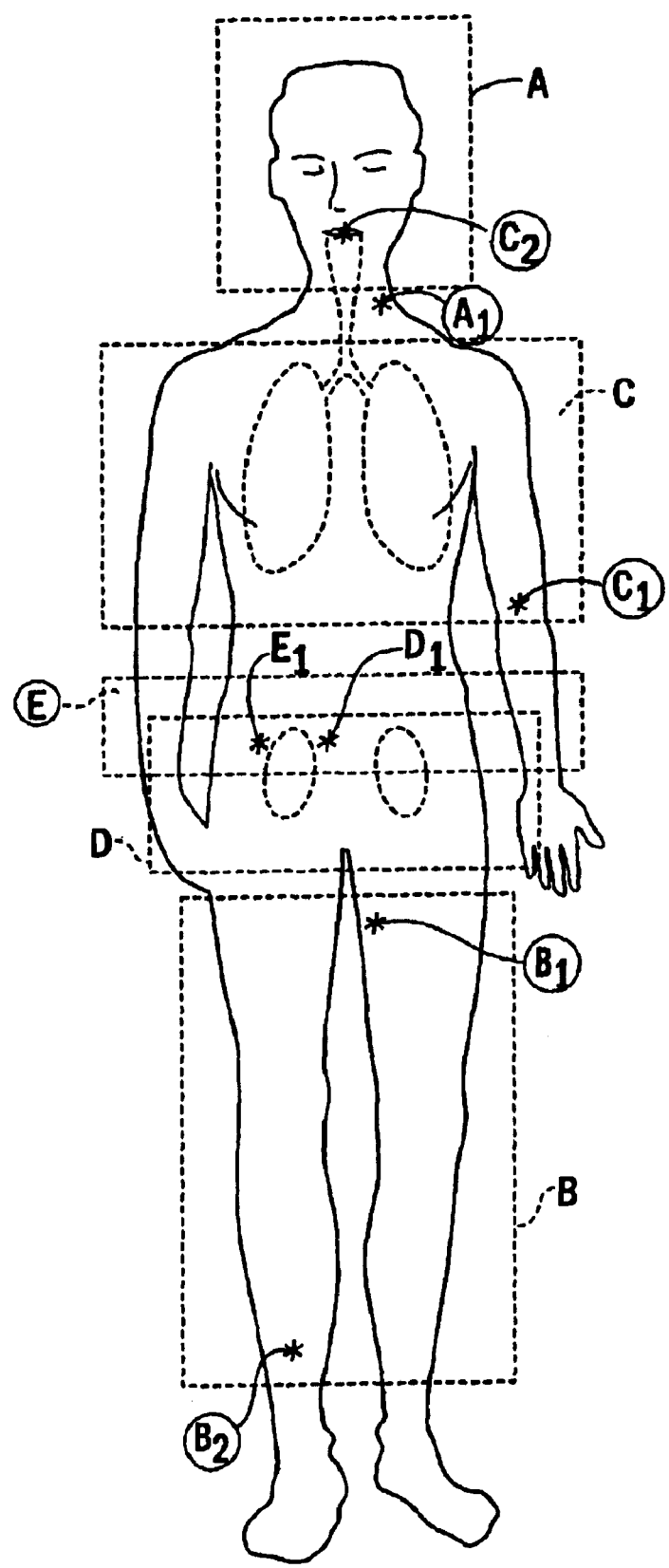
FIG. 1B is a schematic illustration of preferred anatomic injection sites associated with MRI angiographic imaging regions according to the present invention. Region "A" represents the cranium, region "B" represents the lower extremities, region "C" represents the pulmonary vasculature, region "D" represents the renal portion of the circulation system or vasculature, and region "E" represents the hepatic portion of the vasculature. Exemplary injection sites or delivery paths associated with the imaging regions are noted by the numeric subscript. For example, for pulmonary vasculature imaging region represented by the letter "C", a first injection site $C_1$ and a second ventilation delivery path $C_2$ are shown according to the present invention. In contrast, the remainder of the regions are shown with one or more injection sites.

FIG. 1B schematically illustrates suitable injection sites (shown by asterisks located on the body and a corresponding circled letter) and an associated particular tissue, organ, or vasculature target region (shown by dotted line box with and a corresponding letter identification) according to certain embodiments of the present invention.

| Target Region of Interest | Preferred Injection Site |
|---|---|
| Region A Cranium | Neck-Carotid Artery |
| Region B Lower Extremities | Thigh-Femoral Artery |
| Region C Pulmonary | Arm, Vein (preferably in conjunction with ventilated gas) |
| Region D Renal (Kidneys) | Renal Artery |

-continued

| Target Region of Interest | Preferred Injection Site |
|---|---|
| Region E Hepatic (Liver) | Hepatic Wedge |
| Region A Cranium | Right internal juglar artery (IJ) |

For example, as shown by the two circle "C" delivery sites, the pulmonary region preferably employs both an injection site to a vein in the arm to deliver gaseous $^{129}$Xe and an inhalation delivery of polarized gas (the inhalation being either $^{129}$Xe or $^3$He, more preferably $^{129}$Xe). Of course, the present invention is not limited to the injection sites and target regions disclosed above, as additional or alternate sites and additional or alternative target regions can also be employed. Indeed, internal injection or release sites can also be employed such as through the use of special catheters (threaded to the desired injection or delivery site) to deliver gas phase $^{129}$Xe to desired target regions as will be appreciated by one of skill in the art.

Certain embodiments of the present invention are directed to the use of injected gaseous polarized $^{129}$Xe for the detection of pulmonary embolism. In these embodiments, the xenon is injected into a vein, preferably via an intravenous catheter inserted into a vein in the arm and, after a suitable delay, an image of the xenon in the arterial pulmonary circulation can be made to determine if an embolus is present. For example, about 50-100 cc's of gas are injected and after about 5-25 second delay period, preferably about a 5-7 second image delay period (the delay period being measured from the time after injection stops) scanning is initiated. Preferably, the scanning, based on this injection, is completed in less than about 60 seconds, and preferably, in about 10-45, and more preferably in about 10-20 seconds.

Alternatively, a longer delay can be applied between the time of injection and the image data or signal acquisition or collection so that a scan can be made of the gaseous $^{129}$Xe as it enters in the lung resulting from the venous injection, as the gaseous $^{129}$Xe injected in a vein in the arm will subsequently dissolve only to appear or enter into the lung if circulation is not blocked in the pulmonary arteries. In addition, even if the blockage is not severe enough to prevent the $^{129}$Xe which is injected in gas phase from entering the lung, the signal intensity of this transitory $^{129}$Xe in the lung can vary depending on the degree of restriction (brighter signal for smaller restrictions or free passage, and reduced signal intensity in the lung void space for blocked or substantially restricted blood circulation passages).

In certain embodiments, such as for the lung void space image, as is well known to those of skill in the art, suitable contrast mechanisms such as chemical shift, $T_2^*$, diffusion, etc., can be used to distinguish between imaging segments which include the gaseous $^{129}$Xe in the lung and versus (and preferably excludes or extracts) the signal data associated with the $^{129}$Xe still dissolved in blood.

In certain embodiments, the pulmonary circulation image scan based on the gas injection is coupled with a $^{129}$Xe or $^3$He pulmonary ventilation scan. Using a $^{129}$Xe ventilation scan may be preferable, because it allows the same MRI transmit/receive coil to be used for the entire procedure. The ventilation scan can be employed regardless of the dissolution or lung based image rendering methods employed on the gaseous injected polarized $^{129}$Xe. The coupled scan can identify a V/Q (volume versus flow rate in the circulatory system) mismatch and provide a potential diagnostic tool for the clinician. Alternatively, if $^3$He is used for the ventilation image, it is preferred that the chest coil be configured as a "double tuned" coil. That is, the double tuned coil is tuned to operate for both $^3$He and $^{129}$Xe operation.

In addition, it is preferred that the chest coils be configured to be "proton blocked" allowing the MR scanner body coil to be used to make a proton image of the subject in substantially the exact same position as the subject during the V/Q image. Thus, the proton blocked chest coil allows the body coil to obtain supplemental proton-based data image (without the interference of the polarized gas based coil) which can be combined in a signal processor with the V/Q signal data to provide a more detailed diagnostic evaluation of the target region of interest. Of course, the proton-blocked configuration of the gas based imaging coil can be operated with respect to the other gas-based images described herein.

In certain embodiments, the inhalation based image is generated using polarized $^{129}$Xe while the perfusion image is also generated using the injected gaseous polarized $^{129}$Xe. An NMR system with a low field magnet may be used (such as about 0.1 T-0.5 T), and the pulmonary region image may provide increased signal intensity from the NMR resonance signals resulting from both the dissolved and gas phase xenon in the pulmonary region (two peaks, one associated with the RBC's and one with the plasma). Reduction of field strength can sacrifice chemical shift information between the dissolved phase and gas phase xenon in the target region. Nonetheless, the advantage of low-field imaging of $^{129}$Xe in blood is that the separate peaks of $^{129}$Xe in RBCs versus plasma will overlap and yield a larger total signal than at high-field where $^{129}$Xe in blood or plasma is separately excited and imaged.

Alternatively, a larger field magnet (>0.5 T) can be used which separately excites the dissolved phase and gas phase polarized gas present in the region of interest, and two or more data sets are captured via one or more excitation pulses (such as two separate imaging sequences operated at two different excitation frequencies). In this embodiment, due to the chemical shift between the gas and dissolved phase resonance (approximately 200 p.p.m. at 1.5 T), at least two images (both a perfusion and ventilation image) are generated on a patient during the same imaging session ("differential" imaging). A differential image can provide additional diagnostic information over combined phase signals. For example, the differential image can help distinguish between a pulmonary embolus and a ventilation/perfusion defect associated with a structural anomaly as described above.

In operation, for MR images using $^{129}$Xe as both the inhalation and perfusion medium, a first delivery of a first quantity of hyperpolarized gas can be administered to a subject such as via injection. After a suitable, short, delay corresponding to the desired target imaging region (a delay corresponding to the time it takes the hyperpolarized gas to travel to the desired imaging site from the injection site), a scanning sequence can be initiated. For imaging the chest region (or regions affected by the position of the chest during breathing activities), it is preferred that the patient hold his or her breath to help with locational co-registration between images (especially between injection based and ventilation based images). Image signal data associated with the injected polarized gas according to the present invention is obtained before the polarization of the gas has decayed to an undesirable level (preferably within about 1 minute, and more preferably within about 25 seconds from the time of injection). One or more additional quantities of hyperpolarized $^{129}$Xe can be subsequently injected as needed. That is, a series of small injections (or small releases to an in situ catheter) can be made which allow a corresponding series of data collection based on the image signal data associated therewith.

After the injected polarized gas has cleared the target region (or the polarization has decayed to a point where it does not interfere with the ventilation image), the ventilation delivery can commence. That is, a second delivery of a second quantity of hyperpolarized gas is administered. Because the second delivery is an inhalation delivery, the quantity of gas delivered is relatively large compared to the injectable quantity (about 0.75-1.5 liters versus less than about 20-100 cc's depending on the site). In operation, the subject inhales the second quantity and holds his or her breath (typically for about 15 seconds). In certain embodiments, the injection based and ventilation based MR images (or spectroscopic analysis) can be obtained during the same imaging session, reducing co-registration issues associated with relational positioning/re-positioning. In addition, separate (temporally spaced apart from the injections) breath-hold delivery cycles may be used for ventilation images and perfusion directed images, which can then be digitally combined with the injection signal data to provide a more complete image of the region.

In certain embodiments, where the pulmonary region is the target imaging region, the combined image may be based on at least two different administrations of polarized gas: (a) direct injection of polarized gas into a vein and (b) inhalation of polarized gas. These two different administrations can result in three different delivery mechanisms of polarized $^{129}$Xe to the pulmonary (perfusion from the $^{129}$Xe in the blood and tissues delivered from a venous injection to the arterial side of the circulatory system, perfusion into the vasculature from the inhaled gas delivered to the venous side of the circulatory system, and a ventilation image before, during, and/or subsequent to the perfusion image with the same or additional quantities of inhaled gas).

In any event, differential imaging can provide MR images with information which correlates to the total region (lung space, artery and vein, and boundary regions). This technique can produce MR images which allow diagnostic detection of emboli, perfusion defects, ventilation defects, and other circulatory and/or respiratory system problems in the pulmonary vasculature.

In addition, for studies used to evaluate pharmaceutical effectiveness, the gas may be injected without regard to the toxicity or survival outcome. Indeed, the injection of hyperpolarized $^{129}$Xe into a specific target region can allow the efficacy of a pharmaceutical drug, compound, or mixture, or drug therapy aimed at a particular disease or organ function to be evaluated and or confirmed (post mortem) that such drug is actually delivered to the appropriate site and/or that it has an influence on the targeted condition. For example, a treatment directed to cerebral disorders can be evaluated for effectiveness in suitable animal studies by comparing the injected hyperpolarized-gas based image of the brain over time. Similarly the effectiveness of treatment on pulmonary or cardiac functions, blood flow, or neurological conditions and the like, may also be evaluated. In one example, targeted gene therapy directed to increasing blood vessel growth at the heart can be delivered. Subsequently a quantity of $^{129}$Xe gas can be injected to provide NMR signal based on the increased xenon associated with increased blood vessels at the target site to confirm the success of the directed gene therapy.

In addition, it is expected that small quantities of injected hyperpolarized $^{129}$Xe can provide additional safe and effective in vivo diagnostic assistance in evaluating the presence or absence of cancer in mammalian subjects, particularly humans (i.e., cancerous tumor or benign cyst). For example, in vivo cancerous tumors can be characterized by the presence of increased random blood vessel growth (a condition known as angiogenisis). This is in contrast to benign cysts. Taking advantage of this characteristic and the NMR signal information available using direct $^{129}$Xe polarized gas injection, a target in an organ such as a tumor in a breast can be analyzed in vivo. In operation, a needle can be inserted or injected to the suspect region in the breast via conventional MR guided needle placement and $^{129}$Xe can be released threat (along with or in lieu of removing biopsy materials). Signature peaks in spectroscopy signals can indicate the presence of cancer via the increased peak in the signal due to the increased blood (and xenon's solubility therein). In obtaining the signal or images, an appropriate field strength should be used so as to differentiate the peaks associated with xenon in blood versus xenon in fatty tissue as will be appreciated by one of skill in the art. Of course, other contrast mechanisms like chemical shift, $T_2$* and the like, can also be employed to exploit the $^{129}$Xe image signal in the tumor.

Figure 2:
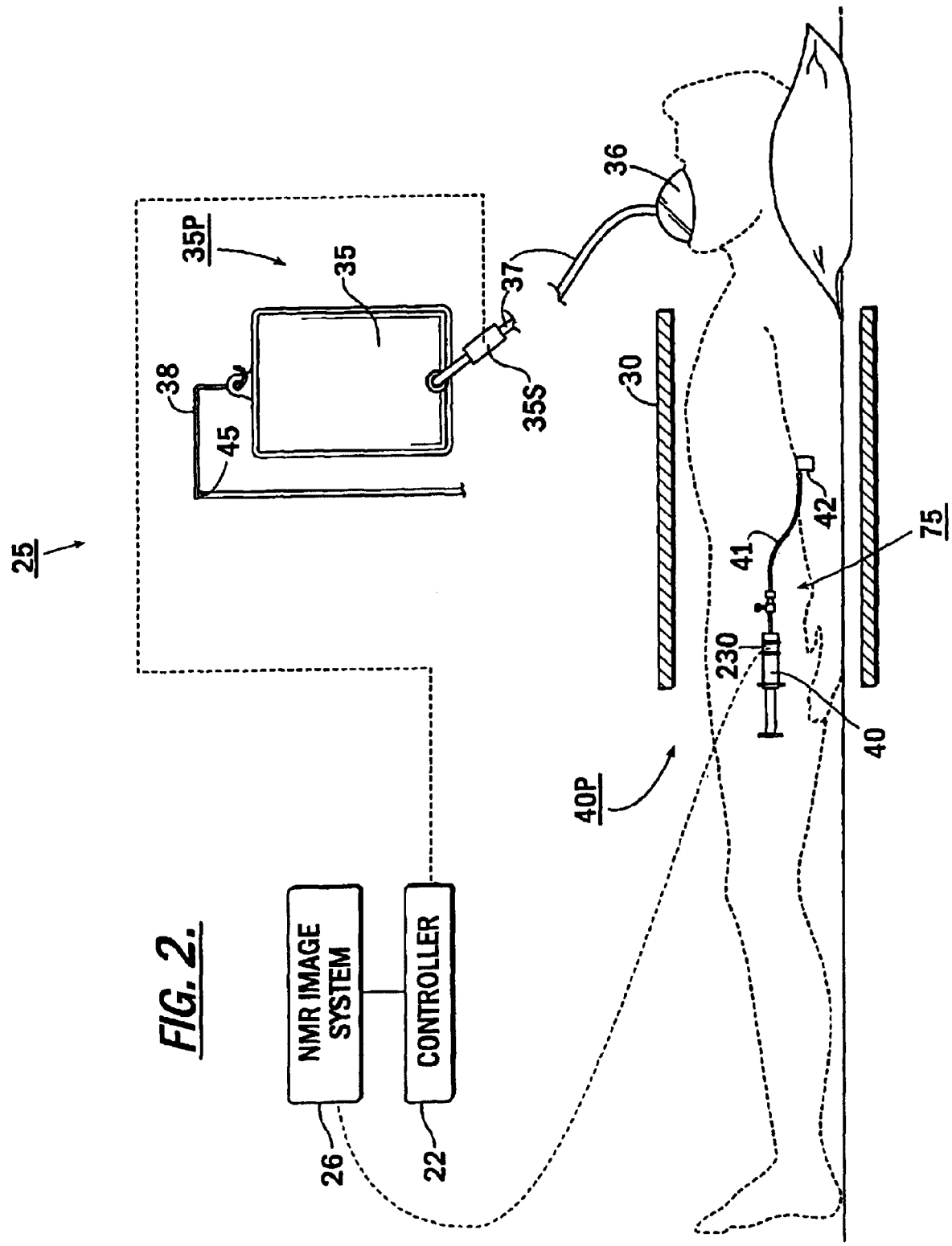
FIG. 2 is a schematic illustration of a MRI system for pulmonary embolism screening according to a preferred embodiment of the present invention. As shown, the subject is receiving two separate doses of hyperpolarized gas, one of which is injected $^{129}$Xe gas and one of which is inhaled gas (ventilated).

Referring to FIG. 2, in a preferred embodiment, a patient is positioned in a MRI system 25 and exposed to a magnetic field associated therewith. The MRI system 25 typically includes an NMR image processing system 26, a super-conducting magnet (not shown), gradient coils (with associated power supplies) (also not shown), an excitation coil (transmit/receive RF coil) 30. Preferably, the coil 30 is configured as Helmholtz pairs oriented at 90 degrees relative to each other (not shown). Of course other configurations can also be used such as Helmholtz coil or a surface coil for imaging near surface regions of the subject. The system also includes a RF amplifier for generating RF pulses set at predetermined frequencies (also not shown). For $^{129}$Xe imaging at 1.5 T field strength, the MRI imaging system 25 is set to operate in the gas-phase at about 17.6 Hz. For high field applications, the dissolved phase excitation frequency is shifted below the gas phase excitation frequency. For example, the dissolved phase excitation frequency is shifted to be about 200 p.p.m. lower than the gas phase excitation frequency (corresponding to the chemical shift). Thus, at 1.5 T, the dissolved phase $^{129}$Xe RF excitation frequency is about 3.52 kHz lower than the associated gas-phase excitation frequency. In yet another preferred embodiment, the imaging method employs a 17.6000 MHz gas phase excitation pulse and an associated dissolved phase excitation pulse of preferably 17.59648 MHz. Of course, the magnet field strength and excitation frequency can vary as is well known to those of skill in the art.

In any event, in operation the RF pulse(s) is transmitted to the patient to excite the nuclei of the polarized $^{129}$Xe. The coil 30 is tuned to a selected frequency range and positioned adjacent the targeted imaging region to transmit the excitation pulses and to detect responses to the pulse sequence generated by the MRI imaging system 25. The coil 30 shown in FIG. 2 is positioned to image the pulmonary vasculature region 12 (FIG. 1A). Preferred coils 30 for standard chest imaging include a wrap-around coil with conductors positioned on both the front and back of the chest. Examples of suitable coils known to those of skill in the art include a bird cage configuration, a Helmholtz pair or quadrature Helmholtz pairs, a surface coil, and a solenoid coil. The RF excitation coil 30 is operably associated with the NMR image processing system 26 for exciting and transmitting image signal information from the polarized gas back to the NMR image processing system 26.

As noted above, once in position, the patient inhales a (predetermined) quantity of polarized $^{129}$Xe gas into the pulmonary region (i e., lungs and trachea). Preferably, after inhalation, the patient holds his or her breath for a predetermined time such as 5-20 seconds. This is described as a "breath-hold" delivery. Examples of suitable ventilation or inhalation delivered "single dose" quantities of polarized gases for breath-hold delivery include 0.5, 0.75, and 1.0 liters of gas. Preferably, the dose at inhalation contains gas with a polarization level above 5%, and more preferably a polarization level above about 20%.

Figure 5:
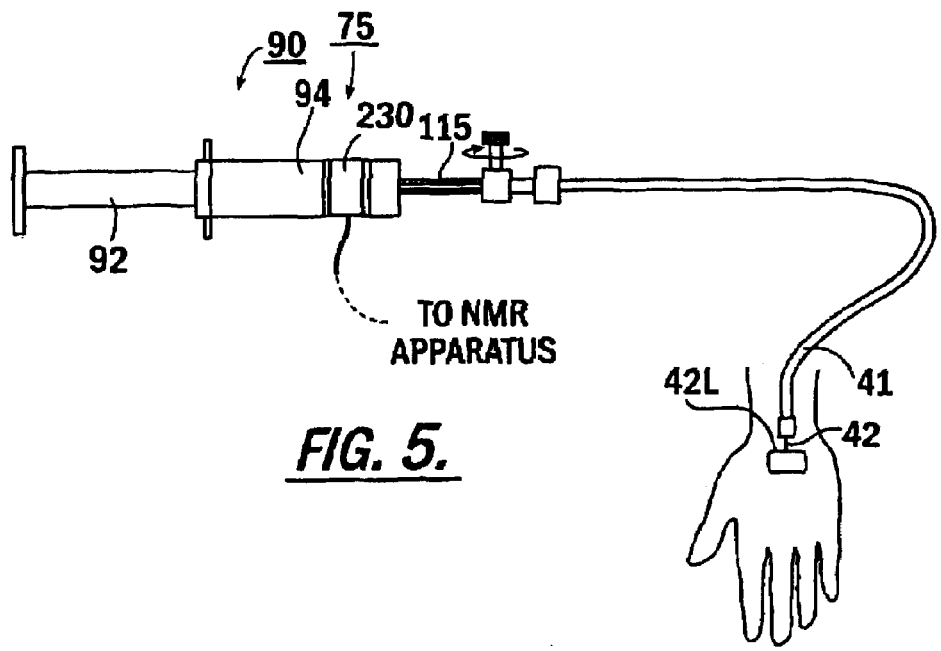
FIG. 5 is a schematic illustration of a controlled gas delivery system according to the present invention.

The MRI imaging system 25 shown in FIG. 2 includes a dual dose delivery system 38. Thus, as shown, the dual dose delivery system 38 preferably includes both an inhalation dose bag polarized gas supply 35 and an injectable gas dose $^{129}$Xe supply 40. Preferably, a non-magnetic support 45 is employed to hold at least the inhalation dose(s) of polarized gas. The inhalation dose bag 35 is suspended from the support 45 and a length of polarization friendly conduit 37 is in fluid communication with the dose bag 35 and a mask 36 positioned over the airways of the subject, so that the subject can inhale the polarized gas, while positioned in the magnet, at the appropriate time. Preferably, the injectable dose 40 is preferably engaged with a catheter or IV 42, and is positioned proximate to the subject to reduce the conduit length 41 necessary to connect the gas to the catheter lumen 42 (IV) inserted into the subject. FIG. 5 illustrates an alternate injection site with the injected gas preferably delivered to the patient at a controlled rate, pressure, and a substantially controlled overall dispensed quantity.

One way to dispense the gas is to employ an inflatable bladder configured and sized to receive a major portion of the injected dose gas bag 40 (preferably configured to enclose the dose bag therein). In operation, at the appropriate predetermined dispensing time in the imaging cycle, a controller directs a compressor to fill the inflatable bladder to exert pressure onto the external walls of the flexible polymer dose bag. Air, gases or other fluids or liquids can also be used to expand the inflatable bladder. Preferably, for preservation of the polarization, deoxygenated water is used to reduce the migration of air into the dose bag. Of course, air can also be used, as the inflatable bladder is preferably configured with discrete channels which are formed of a magnetic contaminant-free material such as rubber, elastomers, or other expandable materials which will act as a shield between the bag walls and the air (i.e., the air does not directly contact the exterior walls of the bag 40). Preferred materials for the dose bag are described in U.S. Pat. No. 6,128,918 and co-pending and U.S. patent application Ser. No. 09/334,400, the contents of which are hereby incorporated by reference as if recited in full herein.

In any event, as the bladder expands, it increases the pressure it exerts onto the dose bag 40. Preferably, the bladder is symmetrically configured with discrete enclosed air (or gas or fluid) channels such that opposing channels contact opposing sides of the bag to facilitate a constant and substantially equal distribution of pressure without the inflatable medium directly contacting the walls of the dose bag 40. In addition, instead of discrete channels 40C, the inflatable bag 40B itself can be sealed and inflate around the enclosed dose bag.

Also, whenever more than one delivery mechanism is employed to introduce polarized gas products to a subject, the MR imaging system 25 can be configured to include an audible or visual alert to coordinate the dispensing of the substances.

Figure 6:
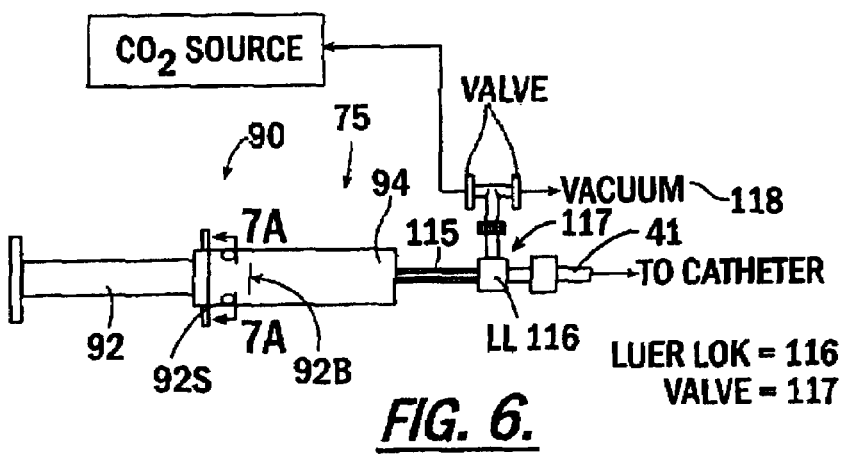
FIG. 6 is a side view of an alternate controlled gas delivery system according to the present invention.
Figure 7A:
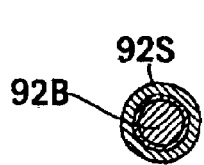
FIG. 7A is a section view of the syringe taken along the line drawn as 7A-7A in FIG. 6.
Figure 7B:
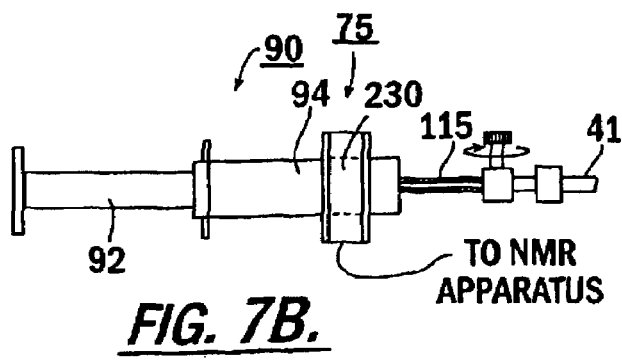
FIG. 7B is a side view of a hyperpolarized gas injection device with a NMR excitation coil mounted thereon according to the present invention.

FIGS. 6, 7A and 7B illustrate another embodiment of a syringe injection delivery system 75 according to the present invention. As shown, the syringe 90 includes a plunger 92, a primary chamber 94, capillary stem 115, and LUER LOK flow member 116 with a valve 117. As shown in FIG. 6, the LUER LOK flow member 116 is connected on one side via the valve 117 to a vacuum system 118. The valve configuration allows a vacuum to be introduced to pull unwanted oxygen from the chamber to prepare the container prior to gas introduction therein.

In the past, high purity/high grade nitrogen has been used to purge the oxygen from the hyperpolarized gas containers to reduce polarization losses attributed thereto. According to a preferred embodiment of the present invention, $CO_2$ gas can be directed into the gas holding chamber and then removed via a vacuum introduced thereto in a "gas-evacuate" cleansing cycle. This $CO_2$ based gas-evacuate container preparation method can remove depolarizing oxygen from the containers. Further, even if residual traces of $CO_2$ remain in the chamber or passages, any $CO_2$ injected with the hyperpolarized gas will be absorbed by the blood relatively quickly as noted above.

As the polarized gas contacts the primary chamber 94, the plunger 92, and the walls of the capillary stem 115 and lumen (during injection), it is preferred that they be configured from a polarization friendly material. As used herein, the term "polarization friendly material" means materials which reduce the contact induced decay or relaxation associated therewith, such as materials which have reduced solubility, permeability, or relaxivity values. Examples of suitable materials will be described further below.

Accordingly, it is preferred that the primary chamber 94 and at least the bottom primary surface 92B of the plunger (the gas contacting surface) be configured from a gas-contacting material which has a low relaxivity for $^{129}Xe$. This material can comprise a high purity metal which is substantially free of ferrous and paramagnetic impurities. As shown in FIG. 7A, the bottom surface of the plunger 92B is formed of a low-relaxivity material and a second peripherally (circumferentially) positioned seal 92S. See co-pending U.S. patent application Ser. Nos. 09/334,400 and 09/528,750, for a discussion of materials, containers, and gas delivery systems, the contents of which are hereby incorporated by reference as if recited in full herein. The sealing material can also be coated with a polarization friendly material or formed of materials and fillers with reduced depolarizing influence.

Exemplary materials for the interior surface of the primary chamber body and/or bottom surface of the plunger material (or other gas contacting surfaces such as capillary stems and conduits/catheters) includes certain polymers such as PE and nylon-6, and high purity glass (preferably high purity aluminosilicates) or quartz (or sol-gel coated surfaces (see e.g., PCT US98/16834 to Cates et al., entitled *Sol-gel Coated Polarization Vessels*), and high purity metallized surfaces (substantially free of ferrous and paramagnetic impurities)). If high purity metal gas contacting surface materials are used, it is preferred that the high purity metal surface be formed from one or more of aluminum, gold, or silver. It is also preferred that any O-rings or seals used be coated with or formed from polarization-friendly materials to protect the gas from contacting potentially depolarizing fillers and other materials used in many commercially available seals. Of course, the lumen 42L (FIG. 5) itself is also preferably formed such that at least the gas-contacting surfaces are coated with a high purity metal.

As noted above, in one embodiment, the syringe 90 also includes a capillary stem 115 which is configured to separate the primary gas chamber 94 of the syringe 75 from the valve 117 (to reduce the exposure to same because outer components such as the valve 117 or conduit 41 can potentially include depolarizing components). As such, the capillary stem 115 typically includes a reduced size diameter passage which extends a distance between the chamber 94 and the LUER LOK flow member 116, valve 117, and other components. Preferably, the capillary stem 115 is formed of an aluminosilicate and is directly formed onto the end of the primary chamber 94. It is also preferred that the capillary stem 115 is sized with a length which is at least about 10% the length of the primary chamber, and more preferably at least 20% the length of the primary chamber. For example, for a 10 ml syringe having a chamber length of about 6 cm, the capillary stem has a corresponding length of about 6 mm. Of course, other configurations can also be used and the present invention is not considered to be limited thereto. For example, optimal or improved capillary stem sizing methods are discussed further below.

In one embodiment, to obtain about a relatively long $T_1$, the container 100 includes a primary gas holding chamber which has a chamber volume which is substantially larger than the volume associated with the capillary stem 115 (the chamber volume is preferably at least an order of magnitude greater volume than the capillary stem volume). In this embodiment, the capillary stem is configured with a length which is about 6.9 cm. One may also configure the radius of the stem such that is at, or less than, about 0.3 cm.

Thus, in producing the injectable product container, the syringe 75 can also be connected to the $CO_2$ source in conjunction with the vacuum source (or separately) to direct $CO_2$ gas into the syringe along the passage 115P in the capillary stem 115 so as to run a series of several gas/evacuation or purge cycles to remove the oxygen and clean the chamber and capillary stem 115. The gas-evacuation preparation method will be discussed further below.

After the gas-evacuate cycle (or purge/pump cycles) the chamber 94 can be finally evacuated and the valve 117 closed in preparation for filling with the hyperpolarized $^{129}Xe$ gas. Of course, the hyperpolarized gas can be directed into the syringe chamber 94 at a later time or at a time proximate to the evacuation step. In any event, once the desired volume of gas is directed into the syringe 75, the valve 117 can be closed and the syringe 75 transported to the patient. A catheter 42 can be positioned and the lumen inserted into the patient in advance of engaging the syringe to the conduit and opening the LUER LOK flow member 116 to release the gas in to the in situ catheter 42 to deliver the gas at the appropriate time.

FIGS. 8A and 8B illustrate yet another system for controlling/and or dispensing hyperpolarized gas to a subject. FIG. 8A illustrates a container 100 with a primary valve 110, a primary gas holding chamber 112, a capillary stem 115, and an expandable member 120. The primary valve 110 moves forward and rearward in response to rotation of the knob 110R to open and close the passage defined by the capillary stem 115 from the first port 116. A second entry port 125 is configured opposing the capillary stem 115 in fluid communication with the primary gas chamber 112. Preferably, a secondary valve 130 operates to open and close the second entry port 125. The expandable member 120 expands into the primary chamber 112 when the valve 130 is opened and fluid is introduced into the second entry port 125. The degree of expansion of the expandable member 120 corresponds to the quantity of fluid introduced through the second port 125. A liquid, gas, or mixture thereof can be used to expand the expandable member 120.

In one embodiment, the expandable member 120 defines a barrier between the polarized gas and the expansion medium; the expansion medium does not directly contact the polarized gas. Any suitable liquid or gas can be used as the expansion medium, and for thin barriers which may allow the medium to travel therethrough, nitrogen or deoxygenated water, or other substantially non-depolarizing fluids can be used as the expansion medium. In addition, because the expandable member does contact the polarized gas, it is preferred that it be formed of a polarization friendly (low relaxivity and low solubility) material for the polarized gas held therein. For example, a material such as LDPE or deuterated HDPE, or more preferably a high purity non-magnetic metal and the like, or other low-relaxivity material which has a low permeability for the hyperpolarized gas held in the chamber may be employed. See co-pending patent application Ser. Nos. 09/163,721 and 09/334,400. The contents of these documents are hereby incorporated by reference as if recited in full herein.

As shown in FIG. 8B, after filling the container 100 at a fill site with a desired quantity of hyperpolarized gas such as $^{129}$Xe through the first entry port 116, an injection means such as a matable conduit or chamber with a direct inject needle/lumen, catheter or IV needle 119, 42L is connected to the first entry port 116. In position, as shown the container 100 can be oriented on its side so that the length of the delivery or polarized gas dispensing path "L" away from the container 100 can be reduced to reduce the potential exposure of the gas to contaminants as it travels therethrough. In the embodiment illustrated, a controller 22 directs an air compressor 47 to inflate the expandable member at a predetermined rate (preferably a constant rate). The primary valve 110 is opened and the polarized gas is allowed to exit the first entry port 116 at a controlled rate into the injection path and into the lumen 42L. In addition, the capillary stem 115 of the container is preferably configured such that once the gas is captured in the primary chamber 112, a major portion of the hyperpolarized gas in the container is isolated away from potentially depolarizing components (such as fittings, valves, and the like) during transport and/or storage as noted above. Of course, other flow control configurations can also be employed. For example, filling a container having a valve in fluid communication with tubing to about 2 atm with polarized $^{129}$Xe. The valve can be opened and the pressure difference directs the gas into the tubing out of the container. Of course, over time, the flow rate due to the pressure differential will drop.

The capillary stem 115 can be formed as an integral part of the valve member 110 or as a separate component. For example, the valve 110 can include a body portion formed of glass such as Pyrex® or the like, and the capillary stem 115 can be directly formed onto an end portion of the valve 110. Alternatively, the capillary stem 115 can also be formed from a glass such as Pyrex® or an aluminosilicate, or other material to extend therefrom as a continuous body co-joined or fused to the lower portion of the valve 110. The valve illustrated in FIGS. 8A and 8B includes a plug portion 110P which longitudinally translates to engage with the lower nozzle end of the valve chamber 110N to close the flow path when the valve is in the closed position. In the reverse, the valve plug 110$p$ moves away from the nozzle end 110$n$ to allow the gas to flow through the capillary stem 115 and the and in (or out) the entry port 116.

Operationally, still referring to FIG. 8B, the capillary stem 115 is configured such that a major portion of the hyperpolarized gas, once in the chamber 112, remains therein when the valve 110 is closed. That is, the dimensions and shape of the capillary stem 115 are such that diffusion of the hyperpolarized gas away from the container chamber 112 is inhibited. Thus, the capillary stem 115 can reduce the amount of exposure for a major portion of the hyperpolarized gas with the valve 110 and any potentially depolarizing components operably associated therewith. In addition, the capillary stem 115 also provides a portion of the gas flow path 22$f$ therethrough. As such, the capillary stem 115 includes an internal passage which is preferably sized and configured in a manner which inhibits the flow of gas from the chamber 112 during storage or transport while also allowing the gas to exit the chamber 112 at its ultimate destination (injection site) without undue or significant impedance.

In sizing a capillary stem (which can be employed with any type of container housing hyperpolarized noble gas (such as that shown in FIG. 6 or 8A or otherwise)) to optimize the $T_1$ of the $^{129}$Xe gas held therein, the following analysis can be used. Generally stated, $T_1$ can be represented by the following equation:

$$T_1 \approx \frac{V_{main} l_c}{2\pi R_c (DR_c + \psi l_c^2)}$$

Reviewing the equation, it will be appreciated that as $T_1 \to \infty$ as $R_c \to 0$. Thus, the "best" capillary radius is none at all. However, this is not practicable. Typically, a certain basic or minimum capillary radius is needed, i.e., sufficiently sized, in order to allow gas to flow in and out of the capillary and for the main chamber to be successfully evacuated. In addition, some design limit can be placed on the "gas conductivity" of the capillary. This aspect will be discussed further below. In any case, once a capillary radius or width has been chosen, the equation above can be used to determine an improved or "optimal" capillary length by differentiating the equation and setting it equal to zero. (Of course, the equations below can be used in the reverse to establish a desired radius based on a particular length).

$$\frac{dT_1}{dl_c} = 0$$

This yields a solution for the optimal capillary length represented by the following equation:

$$l_c = \sqrt{\frac{DR_c}{\psi}}$$

Note that this solution for $l_c$ sets the diffusion component of relaxation in the capillary equal to the surface-induced component of relaxation. Since the assumption of infinite depolarization rate at the end of the capillary is probably overstated, one can adjust (reduce) the determined or calculated capillary length a little shorter.

In order to calculate optimal capillary lengths, relaxivity values or estimates are needed. As a simple estimate, one can consider that an 180 cc spherical chamber of GE180 glass has a relaxation times of about 40 hr for $^3$He and about 2 hr for $^{129}$Xe. Knowing the relationship of "A/V=3/R" for a sphere, one can determine the relaxivity $\psi$ of GE180 glass for both gases. The diffusion coefficients are noted for reference below.

| Gas | $T_1$ | $\psi$ | D |
|---|---|---|---|
| $^3$He | 40 hr | $8.1 \times 10^{-6}$ cm/s | 2.05 cm$^2$/s |
| $^{129}$Xe | 2 hr | $1.7 \times 10^{-4}$ cm/s | 0.065 cm$^2$/s |

The table above illustrates that optimal capillary lengths will be very different for $^{129}$Xe with its smaller diffusion coefficient and much larger relaxivity than $^3$He. Thus, this is preferably taken into account when designing the $^{129}$Xe capillary stem.

For example, if we assume a 1 mm capillary diameter, and use the values of relaxivity above, one can find the following:

|  | D | $l_{opt}$ |
|---|---|---|
| $^3$He | 2.05 cm$^2$/s | 111 cm |
| $^{129}$Xe | 0.065 cm$^2$/s | 4.4 cm |

Figure 11:
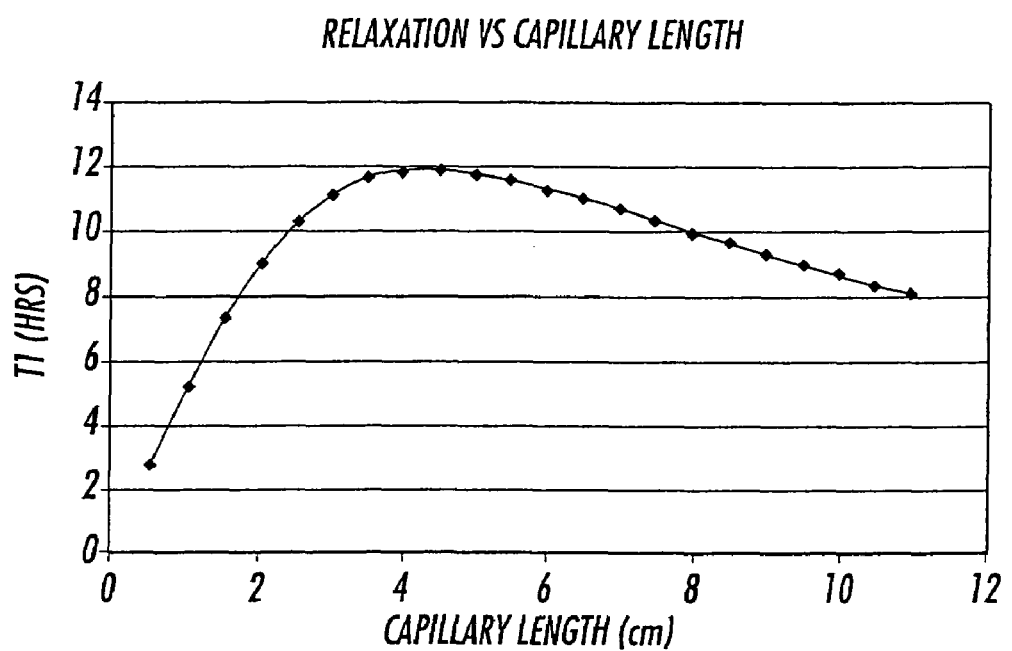
FIG. 11 is a graph which illustrates a relationship which can assess an increased, and preferably, optimum capillary length for containers housing $^{129}$Xe. The graph shows a maximum or optimal $T_1$ obtained at particular length and that for larger or smaller lengths, the $T_1$ is reduced over the $T_1$ obtainable at the optimal length. The same relationship can be used to determine capillary lengths for $^3$He and these lengths will be substantially longer for similar $T_1$'s and similarly sized containers and stem radiuses.

Thus, for a $^{129}$Xe syringe whose main chamber volume is about 20 cm$^3$, using a 4.4 cm capillary of 1 mm diameter can yield a capillary contribution to relaxation of $T_1 \approx 12$ hr. Double the capillary length would yield a $T_1$ of about 9.5 hr, and half the capillary length would yield a $T_1$ of about 9.5 hr. FIG. 11 is a graph which illustrates an optimum capillary length (if one employs a stem with a length which is either larger or smaller than the optimal length, the $T_1$ is reduced over the $T_1$ obtainable at the optimal length)

In a preferred embodiment, the container 100 body (and the syringe body 94) is substantially formed from quartz glass gas contacting surfaces (high purity Si—O$_2$), Pyrex®, aluminosilicate glasses such as GE180, CORNING 1720 or other long $T_1$ life silica based material. Transition glasses may be used to make a transition between glass materials having different thermal expansion coefficients. For example, for containers using multiple types of glass such as Pyrex®, body and GE180 stem or other portion, a transition glass (such as Uranium glass (typically about 35% 235 U)) can be employed to join the two glasses and form the container. A suitable glass valve is available from Kimble Kontes Valves located in Vineland, N.J.

As is shown in FIGS. 7B and 8B, it is also preferred that a small excitation NMR coil 230 be positioned onto the container primary body 94, 112 and operably engaged with the NMR image system 26 via a transmit/receive line 26T. The NMR excitation coil 230 can be in the flow path as shown or located on the side, proximate the exit path (shown as 230a in FIG. 8B). This can allow a calibration measurement to be initiated just prior to dispensing the gas to the subject. Of course, the NMR coil 230 can be positioned in other locations along the body of the container, and the calibration measurement can be taken prior to engagement with the controller 22 or the like. In any event, the injection dose containers of the present invention (such as item 100 in FIG. 8A, items 35 and 40 in FIG. 2, and item 75 in FIG. 6) can allow transport of $^{129}$Xe to the hospital from remote locations (by providing improved $T_1$'s) and can also enable calibration of the gaseous dosage just prior to injection.

FIGS. 8C-8I illustrate alternate embodiments of an injection device according to the present invention. As shown in FIG. 8C, an injector head 300 having a plurality of gas orifices 310 facing in the flow direction can be used to administer the hyperpolarized $^{129}$Xe gas to the subject. The orifices 310 are sized and configured so as to dispense the gas into the subject in a fine dispersion. In certain embodiments, in operation, the injector head 300 is configured to dispense a fine dispersion or spray of gas having microbubble sizes under about 50 µm, and preferably substantially between about 0.5-10 µm.

In certain embodiments, the orifices 310 may have an aperture width or diameter of about 1 nm-50 µm, and preferably a width which is about 10 µm or less such as between about 10 nm-10 µm, between about 0.01-10 µm, or between about 0.01-1 µm to increase the surface area (and decrease the volume) of the bubbles corresponding to the administered gas as it enters the tissue, blood, or selected region of the body. Decreasing the volume and increasing the surface area of the bubbles as they enter the blood stream may promote increased rates of $^{129}$Xe dissolution into the blood (while inhibiting aggregation into undesirable large bubble sizes). A discussion on certain aspects of nanojet configurations can be found in Moseler et al, *Formation, Stability, and Breakup of Nanojets*, Science, Vol. 289, No. 5482, pp. 1165-1169 (18 Aug. 2000); the contents of which are hereby incorporated by reference as if recited in full herein.

The injector head 300 can be formed in or inserted into a distal end portion of an intravenous or intrarterial catheter 340 as shown in FIG. 8D. The injector head 300 may also be positioned at other locations in the hyperpolarized gas flow path (such as at a position with is external of the body upstream of the entry point into the subject in the catheter or in a conduit connected thereto).

As shown in FIG. 8D, the injector head 300 is in fluid communication with a source of hyperpolarized $^{129}$Xe 350 and a pressure source 375. In operation, a constant or variable pressure forces the hyperpolarized $^{129}$Xe to flow through the injector head 300 and out of the orifices 310 to form a gaseous dispersion at a point proximate the entry site of the subject. The constant or variable pressure can be generated with a pressure sufficient to provide a gas flow rate sufficient to create the desired bubble size. Typical flow rates are as described above, such as about 3 cc/s or less (which in certain embodiments administers the gas dose of about 60 cc's over a 20 second injection period). The variable pressure can be provided to generate a pulsatile flow (either via a step function operation or a ramped or gradual variation (increase and/or decrease) over time). The pressure source 375 may be a power injector device, such as those which are well known to those of skill in the art. In operation, a rapid, controlled (pressure and volume) injection of gaseous hyperpolarized $^{129}$Xe can be administered to the subject.

The injector head 300 can be formed into a conduit disposed between the (intravenous or intrarterial) catheter which is configured to pierce the skin of the subject or may be positioned or formed in the catheter itself as noted above.

In certain embodiments, the temperature of the hyperpolarized gas can be adjusted (heated or cooled) prior to ejection through the injector head 300. If cooled, the temperature should be sufficient to assure that the gas remains in the gaseous state at injection. In certain embodiments, the hyperpolarized xenon gas can be heated so that it is at least 70 degrees F., and preferably in the range of about 98.6-105 degrees F., as it travels through the injector head orifices 310. The hyperpolarized gas can be heated by exposing the captured gas to an elevated temperature as it travels along the flow path or by pre-heating a container holding the supply of $^{129}$Xe prior to releasing the hyperpolarized gas into the administration exit flow path. Alternatively, or additionally, the injector head 300 may also be heated. In certain embodiments, heating methods and devices are selected so that, in operation, they do not substantially negatively impact the polarization of the gas (a liquid heated immersion bath for the $^{129}$Xe source container or a supplemental heating container positioned in the flow path, solar or light energy directed to the polarized gas, a flowable heated gas which is directed over the outer surface of the enclosed gas flow path, etc).

As shown in FIGS. 8G and 8H, the injector head 300 can be configured with a convergent nozzle configuration. FIG. 8G illustrates that the injector head 300 itself can have a convergent nozzle profile 301 to direct the gas from the flow path upstream thereof and into to the enclosed nozzle region and out of the orifices 310 positioned at the convergent end thereof. FIG. 8H illustrates that the orifices 310 can be configured in the injector head 300 so that the individual orifices each define a convergent nozzle, identified as a convergent nozzle orifice 310cn (decreases in area from the proximal end to the distal end along the axial direction of flow). Of course the injector head 300 may incorporate both features, convergent nozzle orifices 310cn with a convergent profile 301.

FIG. 8I illustrates that the injector head 300 may include constant area orifices 310ca as well as convergent area nozzle orifices 310cn. In other embodiments, the injector head 300 may be configured with a constant area body and/or the orifices 310 may be formed as only constant area orifices 310ca without convergent area nozzle orifices 310cn (not shown).

FIG. 8G illustrates that the administration can be performed such that an additive can be mixed in situ with the polarized $^{129}$Xe to help form the fine dispersion formulation at ejection from the injector head 300. The additive is a pharmaceutical grade biocompatible substance which is substantially non-depolarizing to the polarized $^{129}$Xe gas. Examples of suitable substances may include blood, plasma, lipids, gases such as $CO_2$ or noble gases including non-hyperpolarized xenon, deuterated substances, or commercially available biomedical contrast agents. See e.g., 60/014,321 and WO 97/37239 to Pines et al. and WO 99/52428 to Johnson et al., the contents of which are hereby incorporated by reference as if recited in full herein.

In certain embodiments, as shown in FIG. 8F, the additive can be an emulsifier which is added to a mixing chamber 375 positioned upstream of the injector head 300 so that the emulsifier is mixed with the hyperpolarized gas to form an emulsified composition of gas as it is extruded or travels through the orifices 310 of the injector head 300. The emulsifer material can be selected such that it is flowable and is able to encapsulate the hyperpolarized gas to promote surface stabilization or to promote the fine dispersion of hyperpolarized gas into the blood. As shown in FIG. 8F, the catheter or conduit 340 can be configured with two separate flow channels 353, 354, which end into the enclosed mixing chamber 375 upstream of the injector head 300. The mixing chamber 375 may include baffles, a venturi, or other mixer components to promote the intermixing of the hyperpolarized gas with the emulsifier (or other additive).

As shown in FIG. 5E, the hyperpolarized gas flow path 353 as well as the additive flow path 354, may include a flow meter 355,455, respectively, or other flow or volume measurement device. In certain embodiments, the additive is controlled so that a substantially lesser amount of additive is used in comparison to the hyperpolarized gas (i.e., 25-40% less than the volume of gaseous polarized $^{129}$Xe). It is noted that the injection system and components described herein may also be suitable for dispensing other gases or agents such as hyperpolarized $^3$He.

The gas contacting surfaces of the injector head 300 can be formed of or coated with suitable materials to inhibit the depolarization of the gas as it travels therethrough. Examples of suitable materials include, but are not limited to, alumminosilicate glass, certain polymer materials or metallic materials or other materials as described herein. Surface coatings, such as a sputter coating of a non-depolarizing material of high purity silver or aluminum. The relaxivity of high purity aluminum for $^{129}$Xe has been recently measured to be about 0.00225 cm/min. Metals other than aluminum which can be used include indium, gold, zinc, tin, copper, bismuth, silver, niobium, and oxides thereof. Preferably, "high purity" metals are employed (i.e., metals which are substantially free of paramagnetic or ferrous impurities) because even minute amounts of undesirable materials or contaminants may degrade the surface. Preferably, the metal is chosen such that it is well below 1 ppm in ferrous or paramagnetic impurity content.

As noted above, because paramagnetic oxygen can be destructive to the polarization of the polarized gas, it is preferred that any syringe, dose bags or other gas containers or gas contacting components such as conduit, catheters, injector heads, mixing chambers, and the like, be preconditioned, i.e., carefully cleaned of magnetic impurities and purged of paramagnetic oxygen. That is, any gas contacting containers or surfaces are processed to reduce or remove the paramagnetic gases such as oxygen from within the chamber and container walls.

It is preferred that the containers be prepared as briefly discussed above. For containers made with rigid substrates, such as Pyrex®, UHV vacuum pumps can be connected to the container to extract the oxygen. However, a roughing pump can also be used which is typically cheaper and easier than the UHV vacuum pump based process for both resilient and non-resilient containers. Preferably, for resilient dose bags, the bags are processed with several purge/pump cycles, e.g., pumping at or below 20 mtorr for one minute, and then directing clean buffer gas (such as $CO_2$) into the container at a pressure of about one atm or until the bag is substantially inflated. The oxygen partial pressure is then reduced in the container. This can be done with a vacuum but it is preferred that it be done with $CO_2$ (at least for the injection containers). Once the oxygen realizes the partial pressure imbalance across the container walls, it will outgas to re-establish equilibrium. Stated differently, the oxygen in the container walls is outgassed by decreasing the partial pressure inside the container chamber. Typical oxygen solubilities are on the order of 0.01-0.05; thus, 95-99% of the oxygen trapped in the walls will convert to a gas phase. Prior to use or filling, the container is evacuated, thus harmlessly removing the gaseous oxygen. Unlike conventional rigid containers, polymer bag containers can continue to outgas (trapped gases can migrate to the chamber because of pressure differentials between the outer surface and the inner surface) even after the initial purge and pump cycles. Thus, care should be taken to reduce this behavior especially when the final filling is not temporally performed near the preconditioning of the container. Preferably, for bags or resilient containers, a quantity of clean filler gas is directed into the bag (to substantially equalize the pressure between the chamber and ambient conditions) and sealed for storage in order to reduce the amount of further outgassing that may occur when the bag is stored and exposed to ambient conditions. This should substantially stabilize or decrease any further outgassing of the polymer or container wall materials. In any event, the filler gas is preferably removed (evacuated) prior to final filling with the hyperpolarized gas.

It is also preferred that the container, syringe, conduit, catheter, injector device, dose bag, or the like, be sterilized prior to introducing the hyperpolarized product therein. As used herein the term "sterilized" includes cleaning containers and contact surfaces such that the container is sufficiently clean to inhibit contamination of the product such that it is suitable for medical and medicinal purposes. In this way, the sterilized container allows for a substantially sterile and non-toxic hyperpolarized product to be delivered for in vivo introduction into the patient. Suitable sterilization and cleaning methods are well known to those of skill in the art.

The injectable dose is configured as a smaller quantity gas phase product than the inhalation dose as described above. The inhalation dose can be mixed with other inert gases such as nitrogen or other biocompatible fluids to help disperse or atomize the gas in the body (typically in the blood stream). As described above, subsequent to inhalation, at least a portion of the inhaled polarized gas enters into a dissolved state which enters the pulmonary arterial vasculature, including the boundary tissue, cells, membranes, and pulmonary blood vessels. Thus, a substantial amount of the dissolved polarized $^{129}$Xe ultimately enters the blood stream with an associated perfusion rate and cycles to the left atrium via the pulmonary vein, then to the left ventricle and out through the aorta.

Dissolved phase $^{129}$Xe can have a relatively short relaxation time, Ti, generally thought to be due to the presence of oxygen and due to paramagnetic deoxyhemoglobin in the blood compared to $^{129}$Xe which remains in the gaseous phase in the blood. In addition, even within a subject's own circulatory system different $T_1$'s will be exhibited. For example, $T_1$ for substantially fully oxygenated human cell membranes (the systemic arterial portion) will have a longer $T_1$ than the systemic venous portion. That is, the $T_1$ of the polarized gas in the systemic venous portion will be less than the $T_1$ of the polarized gas in the systemic artery portion of the circulatory system which is more oxygenated than the systemic venous portion.

As is also known to those of skill in the art, the polarized $^{129}$Xe also has an associated transverse relaxation time, $T_2^*$. In the bloodstream, the non-dissolved as well as the dissolved phase can have associated $T_2^*$ which is acceptable to obtain signal or images. Indeed, the $^{129}$Xe remaining as a gas in human blood will tend to exhibit longer $T_2^*$'s than that dissolved in human blood. Taking advantage of this characteristic, particularly for gas-phase based imaging (especially for $T_2^*$'s which are greater than at least about 30 milliseconds), multi-echo acquisition methods may be used. As will be appreciated by those of skill in the art, examples of suitable multi-echo methods include Echo Planar Imaging ("EPI"), Rapid Acquisition with Relaxation Enhancement ("RARE"), FSE ("Fast Spin Echo"), Gradient Recalled Echoes ("GRE"), and BEST. Examples of some suitable pulse sequences can be found in an article by John P. Mugler, III, entitled *Gradient-Echo MR Imaging*, RSNA Categorical Course in Physics: The Basic Physics of MR Imaging, 1997; 71-88. For example, the article illustrates an example of a standard single RF spin-echo pulse sequence with a 90 degree excitation pulse and a 180 degree refocusing pulse. $G_P$ is a phase-encoded gradient, $G_R$ is the readout gradient, $G_S$ is the section-select gradient, and RF is the radio frequency. The article also illustrates a Gradient Recalled Echo pulse sequence (GRE) with a flip angle α and a Rapid Acquisition with Relaxation Enhancement (RARE) pulse sequence as well as a single shot Echo Planar Imaging (EPI) pulse sequence with gradient recalled echoes.

Figure 9:
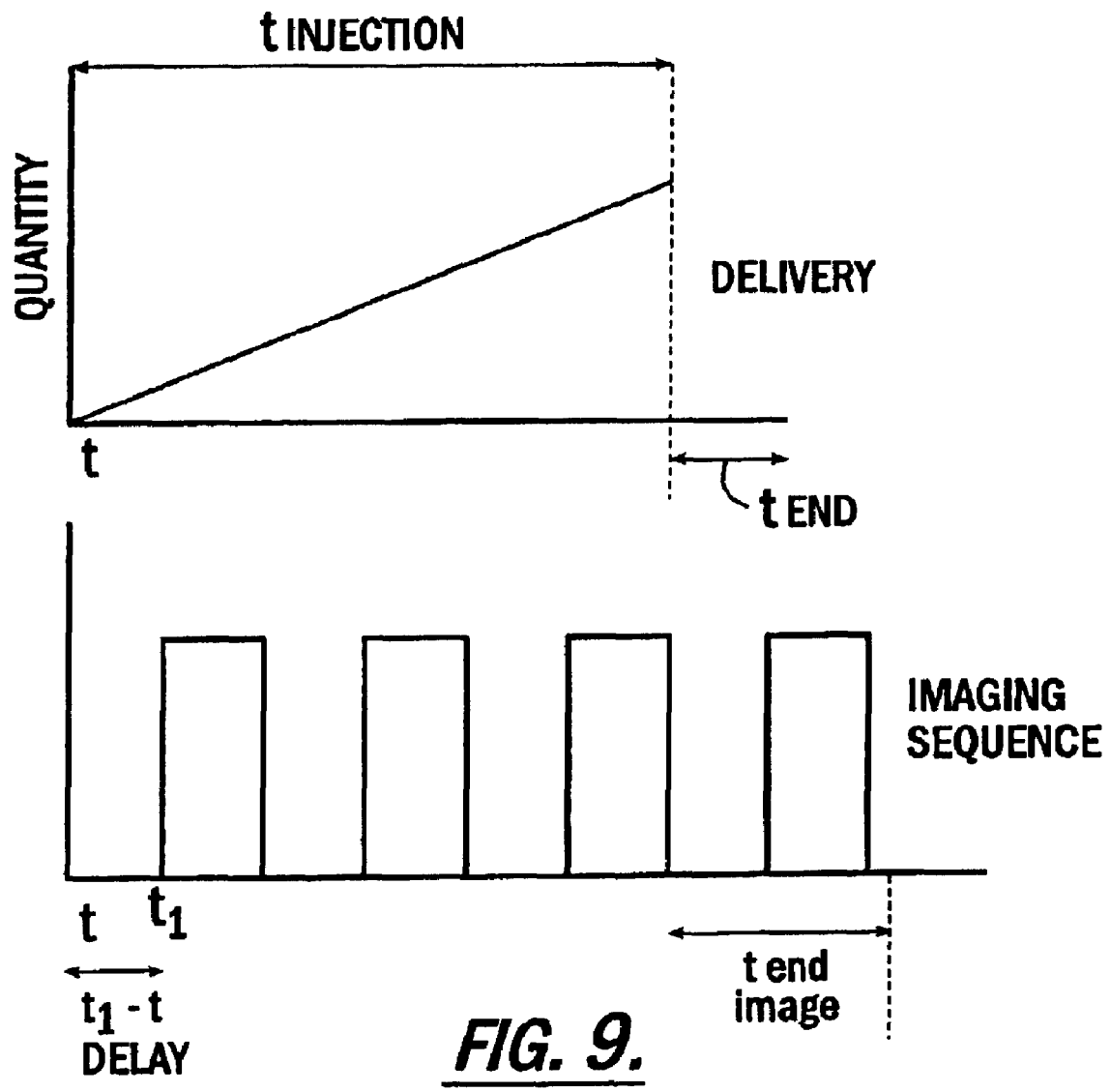
FIG. 9 is a graph of a timing sequence of a quantity of injected gas and a MRI pulse imaging sequence according to a preferred embodiment of the present invention.

FIG. 9 is a graph of one potential timing sequence which may be used and shows the delivery time of the injected gas ($t_{inj}$) and a MRI pulse imaging sequence according to one embodiment of the present invention. The imaging sequence illustrates a relatively long injection time during which a plurality of short small flip angle (below about 45 degrees, and more preferably below about 20 degrees) excitation pulses are directed at the target region. The exciation pulses begin shortly after the start of the injection (t-$t_1$) and end shortly after the injection ends ($t_{end\ image}$). In any case, the end of clinically useful signal generation associated with the injected hyperpolarized gas which is suitable for imaging is typically about 25 seconds after the gas injection has ended, as the polarization of the gas has effectively decayed by this time. Of course, the choice of which flip angle and imaging procedure to use can depend on how many echoes can be done and how many phase encodes steps are pursued. For single echo acquisitions and increased (or optimal) SNR, having 128 phase encodes, a flip angle of about 5.1 degrees can be used.

It will be appreciated that at high magnetic field strength, it is possible to obtain increased image signal strength based on the dissolved phase direct injection polarized gas as well as the signal strength from gas phase ventilation in the lung. This can provide improved signal image resolution associated with the injected gas. It will also be appreciated that there will be separate and distinctly resolvable excitation resonances associated with the (dissolved) versus ventilation (gas) imaging data signals. In contrast, at low magnetic field strengths, the separate resonances distinct at high fields, may overlap to provide an apparent increased image signal strength associated with both the dissolved and gas phase polarization.

Preferably, particularly for longer injection times (a delivery administered over a time which is greater than about 2.5 seconds), one or more small flip angle pulses can be employed to excite the polarized gas in the target region (such as the vasculature) to selectively destroy the polarization in a more localized image acquisition. As used herein, the term "small angle" means less than about 45 degrees.

Preferably, the gas injection sized quantities of hyperpolarized $^{129}$Xe are formulated as istopically enriched polarization gaseous products.

EXAMPLES

Figure 10A:
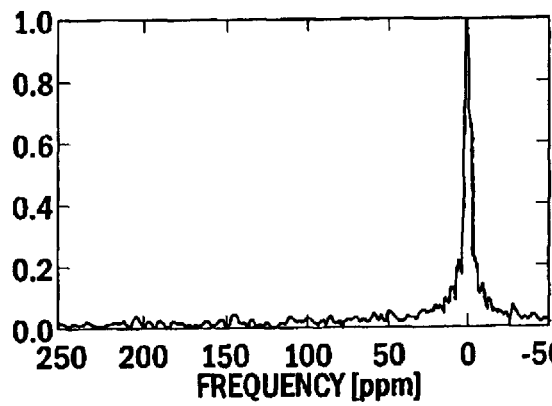
FIGS. 10A-10P are graphs of NMR spectra obtained about every 0.5 seconds via a whole body imager based on about a 3 cc polarized $^{129}$Xe gas injection into the vein of a rabbit (total of elapsed time from FIG. 10A to 10P being about 8 seconds). The graphs illustrate that the gas remained substantially in the gas phase (substantially insoluble as it traveled through the bloodstream during the image acquisition). The signal strength at 8 seconds (FIG. 10P) being about 0.65 that of the original signal (FIG. 10A).
Figure 10B:
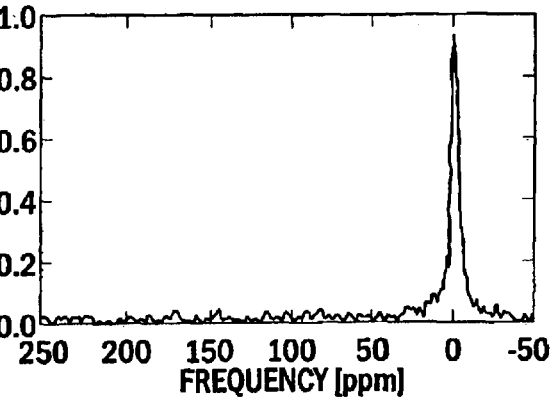
Figure 10C:
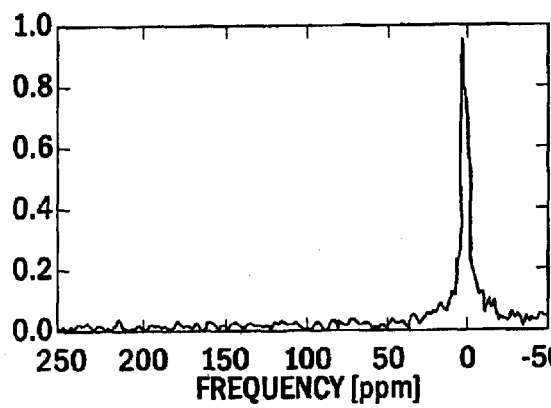
Figure 10D:
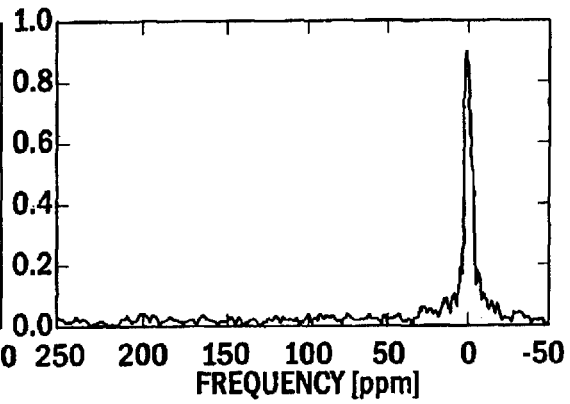
Figure 10E:
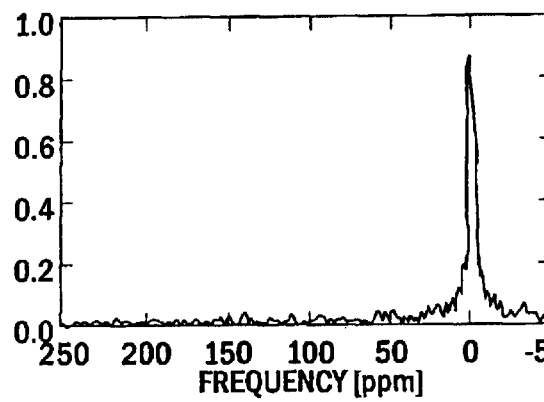
Figure 10F:
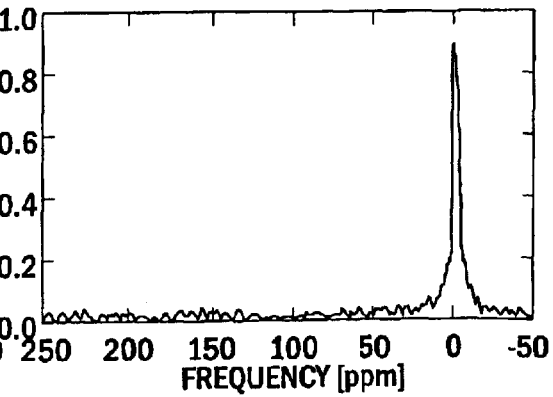
Figures 10G, 10H:
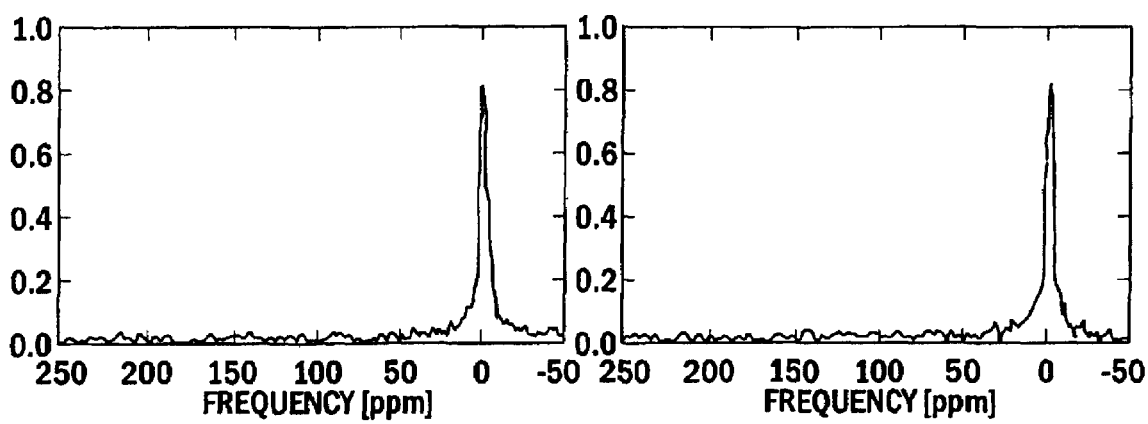
Figure 10I:
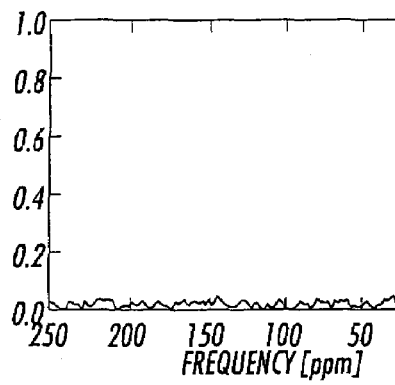
Figure 10J:
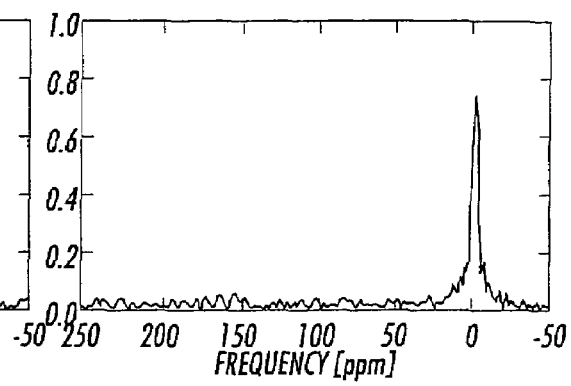
Figure 10K:
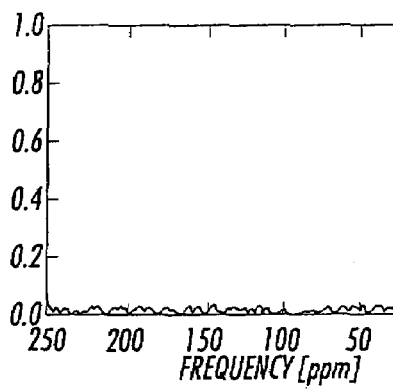
Figure 10L:
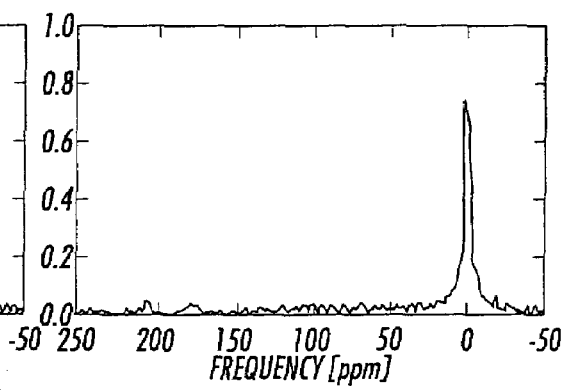
Figures 10M, 10N:
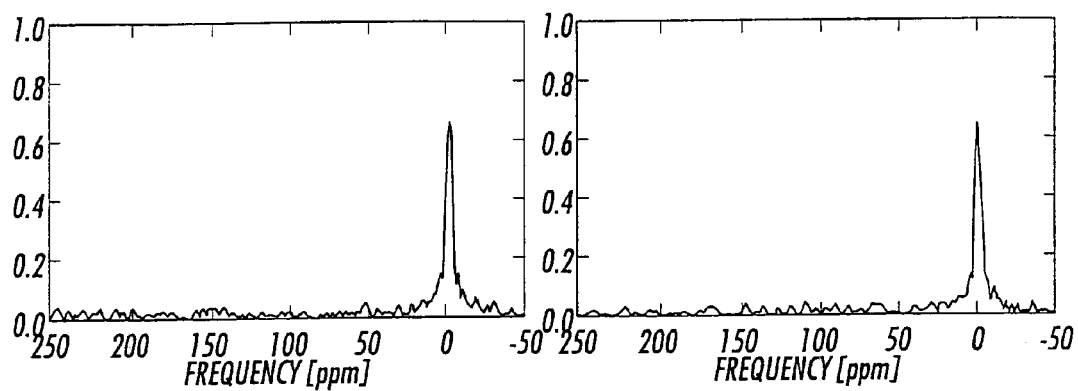
Figures 10O, 10P:
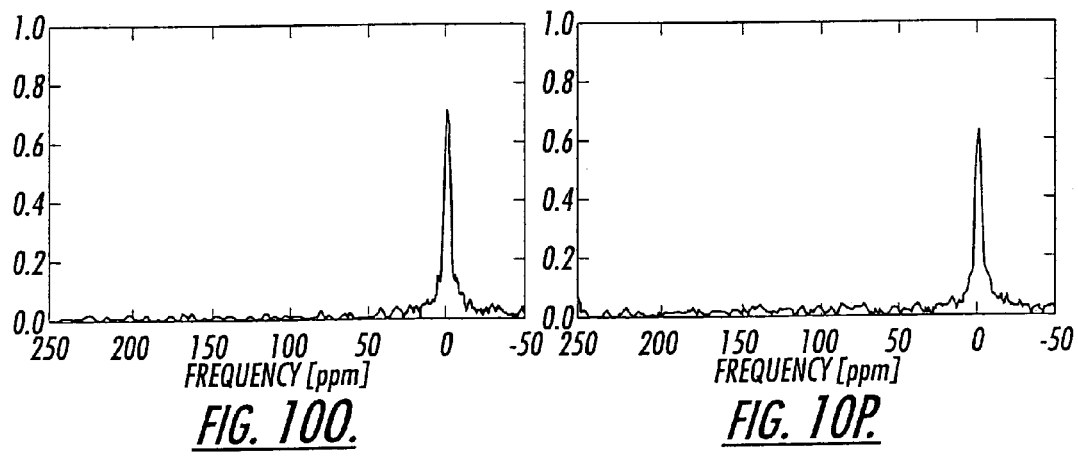

FIGS. 10A-10P are graphs of NMR spectra obtained about every 0.5 seconds with a 20 degree excitation pulse via a whole body imager based on about a 3 cc polarized $^{129}$Xe gas injection into the vein of a rabbit (total of elapsed time from FIGS. 10A to 10P being about 8 seconds). The rabbit survived the experiment. The graphs illustrate that the gas remained substantially in the gas phase (substantially non-dissolved or insoluble in the bloodstream as it traveled through the bloodstream during the image acquisition). The signal strength at 8 seconds (FIG. 10P) being about 0.65 that of the original signal (FIG. 10A). The rabbit was placed in a whole body imager so that the exact location of the signal within the rabbit's body is not disclosed in the spectra. It is noted that a large quantity of the injected gas remained in the gas phase upon injection, most likely due to the size of the lumen used, about 0.5 mm.

It is also notable that the $T_1$ of the gas in the blood is relatively long, at least about 20 seconds (for comparison, the $T_1$ of gas dissolved in blood is typically less than 20 seconds, such as about 4-6 seconds depending on oxygenation).

In summary, it is anticipated that diagnostic images can be obtained according to the present invention for desired target organs or systems, such as but not limited to, the kidneys, the brain or cranium region for cerebral assessment (grey/white matter/blood), the liver, spleen, intestines, lower extremity blood circulation, tumor assessment (oxygen tension) and coronary artery restrictions/blood flow and other regions of interest.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of evaluating the efficacy of targeted drug therapy, comprising the steps of:
   delivering a quantity of predetermined gene treatment preparation or pharmaceutical drug in vivo into a mammalian subject having a target site and a treatment condition, wherein said treatment condition is one of a cardiac condition and a pulmonary condition;
   injecting a predetermined quantity of gaseous phase hyperpolarized $^{129}$Xe in vivo into a mammalian subject such that the hyperpolarized gas is delivered to the target site in gaseous or dissolved form;
   generating a NMR image or spectroscopic signal of the target site associated with the injected hyperpolarized $^{129}$Xe gas; and
   evaluating the NMR image or spectroscopic signal to evaluate the efficacy of the gene treatment or drug on the treatment condition.

2. A method according to claim 1, further comprising the step of acquiring at least two sets of data, the data representing two temporally spaced apart points in time, to evaluate if the treatment condition is influenced by the drug or gene therapy introduced in said delivering step.

3. A method according to claim 1, further comprising the step of evaluating whether the drug is properly delivered to the target site.

4. A method according to claim 1, wherein said at least two data sets correspond with a hyperpolarized 129Xe gas NMR signal data acquisition obtained both before said delivering step and after said delivering step.

5. A method according to claim 2, further comprising at least one of adjusting the quantity or formulation of the drug and confirming the proper delivery to the target site.

6. A method according to claim 1, wherein the treatment condition is one of cardiac function and pulmonary function, and wherein the target site is selected so as to administer polarized $^{129}$Xe gas to a region representative of that condition.

* * * * *